United States Patent
Brenner

(10) Patent No.: US 9,194,001 B2
(45) Date of Patent: *Nov. 24, 2015

(54) METHODS AND COMPOSITIONS FOR TAGGING AND IDENTIFYING POLYNUCLEOTIDES

(71) Applicant: Population Genetics Technologies Ltd, Cambridge (GB)

(72) Inventor: Sydney Brenner, Ely (GB)

(73) Assignee: Population Genetics Technologies Ltd., Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/630,566

(22) Filed: Feb. 24, 2015

(65) Prior Publication Data

US 2015/0240302 A1 Aug. 27, 2015

Related U.S. Application Data

(60) Continuation of application No. 13/852,943, filed on Mar. 28, 2013, now Pat. No. 9,018,365, which is a continuation of application No. 13/466,894, filed on May 8, 2012, now Pat. No. 8,470,996, which is a continuation of application No. 13/425,215, filed on Mar. 20, 2012, now Pat. No. 8,318,433, which is a continuation of application No. 13/211,125, filed on Aug. 16, 2011, now Pat. No. 8,168,385, which is a continuation of application No. 12/111,043, filed on Apr. 28, 2008, now Pat. No. 8,148,068, which is a division of application No. 11/176,927, filed on Jul. 7, 2005, now Pat. No. 7,393,665, which is a continuation-in-part of application No. 11/055,187, filed on Feb. 10, 2005, now Pat. No. 7,217,522.

(60) Provisional application No. 60/662,167, filed on Mar. 16, 2005.

(51) Int. Cl.
C12Q 1/68 (2006.01)
C12N 15/10 (2006.01)
C12P 19/34 (2006.01)

(52) U.S. Cl.
CPC .......... *C12Q 1/6874* (2013.01); *C12N 15/1065* (2013.01); *C12N 15/1093* (2013.01); *C12P 19/34* (2013.01); *C12Q 1/6827* (2013.01); *C12Q 1/6837* (2013.01); *Y10T 436/143333* (2015.01)

(58) Field of Classification Search
None
See application file for complete search history.

(56) References Cited

U.S. PATENT DOCUMENTS

| | | |
|---|---|---|
| 4,942,124 A | 7/1990 | Church |
| 5,149,625 A | 9/1992 | Church |
| 5,451,505 A | 9/1995 | Dollinger |
| 5,635,400 A | 6/1997 | Brenner |
| 5,708,153 A | 1/1998 | Dower et al. |
| 5,770,358 A | 6/1998 | Dower et al. |
| 5,776,737 A | 7/1998 | Dunn |
| 5,846,719 A | 12/1998 | Brenner et al. |
| 5,863,722 A | 1/1999 | Brenner |
| 5,935,793 A | 8/1999 | Wong |
| 5,981,176 A | 11/1999 | Wallace |
| 6,060,596 A | 5/2000 | Lerner et al. |
| 6,352,828 B1 | 3/2002 | Brenner |
| 6,440,667 B1 | 8/2002 | Fodor et al. |
| 6,458,530 B1 | 10/2002 | Morris et al. |
| 8,148,068 B2 | 4/2012 | Brenner |
| 8,168,385 B2 * | 5/2012 | Brenner .................. 435/6.11 |
| 8,318,433 B2 * | 11/2012 | Brenner .................. 435/6.11 |
| 8,470,996 B2 * | 6/2013 | Brenner .................. 536/24.3 |
| 2003/0049616 A1 | 3/2003 | Brenner et al. |
| 2003/0050453 A1 | 3/2003 | Sorge |
| 2003/0096239 A1 | 5/2003 | Gunderson et al. |
| 2003/0207300 A1 | 11/2003 | Matray et al. |
| 2004/0018549 A1 | 1/2004 | Sheppard et al. |

(Continued)

FOREIGN PATENT DOCUMENTS

| | | |
|---|---|---|
| JP | 07313198 | 12/1995 |
| WO | WO9641011 | 12/1996 |

(Continued)

OTHER PUBLICATIONS

Brenner, et al., "In vitro cloning of complex mixtures of DNA on microbeads: physical separation of differentially expressed cDNAs", Proc Natl Acad Sci U S A. Feb. 15, 2000;97(4):1665-70.

(Continued)

*Primary Examiner* — James Martinell
(74) *Attorney, Agent, or Firm* — James S. Keddie; Bozicevic, Field & Francis, LLP

(57) ABSTRACT

The invention provides methods and compositions for attaching oligonucleotide tags to polynucleotides for the purpose of carrying out analytical assays in parallel and for decoding the oligonucleotide tags of polynucleotides selected in such assays. Words, or subunits, of oligonucleotide tags index submixtures in successively more complex sets of submixtures (referred to herein as "tiers" of submixtures) that a polynucleotide goes through while successive words are added to a growing tag. By identifying each word of an oligonucleotide tag, a series of submixtures is identified including the first submixture that contains only a single polynucleotide, thereby providing the identity of the selected polynucleotide. The analysis of the words of an oligonucleotide tag can be carried out in parallel, e.g. by specific hybridization of the oligonucleotide tag to its tag complement on an addressable array; or such analysis can be carried out serially by successive specific hybridizations of labeled word complements, or the like.

13 Claims, 9 Drawing Sheets

(56) References Cited

U.S. PATENT DOCUMENTS

| | | |
|---|---|---|
| 2004/0023267 A1 | 2/2004 | Morris |
| 2004/0058373 A1 | 3/2004 | Winkler et al. |
| 2004/0110191 A1 | 6/2004 | Winkler et al. |
| 2004/0209299 A1 | 10/2004 | Pinter et al. |
| 2004/0259118 A1 | 12/2004 | Macevicz |
| 2006/0008824 A1 | 1/2006 | Ronaghi et al. |
| 2006/0019304 A1 | 1/2006 | Hardenbol et al. |

FOREIGN PATENT DOCUMENTS

| | | |
|---|---|---|
| WO | WO9831833 | 7/1998 |
| WO | WO9859066 | 12/1998 |
| WO | WO9928505 | 6/1999 |
| WO | WO02056014 | 7/2002 |
| WO | WO02061140 | 8/2002 |
| WO | WO02061143 | 8/2002 |
| WO | WO02061145 | 8/2002 |
| WO | WO02064835 | 8/2002 |
| WO | WO02097113 | 12/2002 |
| WO | WO2005068656 | 7/2005 |
| WO | WO2005080604 | 9/2005 |

OTHER PUBLICATIONS

Church, et al., "Multiplex DNA Sequencing", Science, 1988, 240:185-8.

Crick, et al., "Codes Without Commas", Proc Natl Acad Sci U S A. May 15, 1957;43(5):416-21.

Gronostajski, "Site-specific DNA binding of nuclear factor I: effect of the spacer region", Nucleic Acids Res. Jul. 24, 1987;15(14):5545-59.

Gunderson, et al., "Decoding randomly ordered DNA arrays", Genome Res. May 2004;14(5):870-7.

Hensel, et al., "Simultaneous identification of bacterial virulence genes by negative selection", Science. Jul. 21, 1995;269(5222):400-3.

Miner, et al., Miner, et al. "Molecular barcodes detect redundancy and contamination in hairpin-bisulfite PCR", Nucleic Acids Res. Sep. 30, 2004;32(17):e135.

Ohlmeyer, et al., "Complex synthetic chemical libraries indexed with molecular tags", Proc Natl Acad Sci U S A. Dec. 1, 1993;90(23):10922-6.

Qiu, et al., "DNA sequence-based "bar codes" for tracking the origins of expressed sequence tags from a maize cDNA library constructed using multiple mRNA sources", Plant Physiol. Oct. 2003;133(2):475-81.

Shoemaker, et al., "Quantitative phenotypic analysis of yeast deletion mutants using a highly parallel molecular bar-coding strategy", Nat Genet. Dec. 1996;14(4):450-6.

Sobin et al., "Solid phase capturable dideopynucleotides for multiplex genotyping using mass spectrometry", Nucleic Acids Research, 2002, vol. 30, nol. 16, pp. e85 (6 pgs.).

Wang, et al., "Balanced-PCR amplification allows unbiased identification of genomic copy changes in minute cell and tissue samples", Nucleic Acids Res. May 21, 2004;32(9):e76.

Wood et al., "Isolation and Purification of Large DNA Restriction Fragments from Agarose Gels", Current Protocols in Molecular Biology (2002) pp. 2.61-2.6.12.

\* cited by examiner

Combinatorial Tag With No "Commas"

Combinatorial Tag With "Commas" Between Words

Combinatorial Tag With "Commas" at Each End

Combinatorial Tag With "Commas-less" Property

| | | | | | Melting Temperatue | | |
| | | | | | Basic | Salt Adjusted | Nearest Neighbor |
|---|---|---|---|---|---|---|---|
| gtcta | tgtca | cttgt | tcitt | acaga | 53 | 61 | 52 |
| tgtca | tgtca | cttgt | tcitt | acaga | 53 | 61 | 54 |
| acaga | tgtca | cttgt | tcitt | acaga | 53 | 61 | 54 |
| cagaa | tgtca | cttgt | tcitt | acaga | 53 | 61 | 53 |
| aicat | tgtca | cttgt | tcitt | acaga | 51 | 59 | 52 |
| gaact | tgtca | cttgt | tcitt | acaga | 53 | 61 | 53 |
| cttgt | tgtca | cttgt | tcitt | acaga | 53 | 61 | 53 |
| tcitt | tgtca | cttgt | tcitt | acaga | 51 | 59 | 52 |
| gtcta | gtcta | cttgt | tcitt | acaga | 53 | 61 | 52 |
| gtcta | acaga | cttgt | tcitt | acaga | 53 | 61 | 52 |
| gtcta | cagaa | cttgt | tcitt | acaga | 53 | 61 | 52 |
| gtcta | aicat | cttgt | tcitt | acaga | 51 | 59 | 51 |
| gtcta | gaact | cttgt | tcitt | acaga | 53 | 61 | 53 |
| gtcta | cttgt | cttgt | tcitt | acaga | 53 | 61 | 52 |
| gtcta | tcitt | cttgt | tcitt | acaga | 51 | 59 | 51 |
| gtcta | tgtca | gtcta | tcitt | acaga | 53 | 61 | 52 |
| gtcta | tgtca | tgtca | tcitt | acaga | 53 | 61 | 52 |
| gtcta | tgtca | acaga | tcitt | acaga | 53 | 61 | 52 |
| gtcta | tgtca | cagaa | tcitt | acaga | 53 | 61 | 52 |
| gtcta | tgtca | aicat | tcitt | acaga | 51 | 59 | 51 |
| gtcta | tgtca | gaact | tcitt | acaga | 53 | 61 | 53 |
| gtcta | tgtca | tcitt | tcitt | acaga | 51 | 59 | 51 |
| gtcta | tgtca | cttgt | gtcta | acaga | 54 | 63 | 54 |
| gtcta | tgtca | cttgt | tgtca | acaga | 54 | 63 | 54 |
| gtcta | tgtca | cttgt | acaga | acaga | 54 | 63 | 54 |
| gtcta | tgtca | cttgt | cagaa | acaga | 54 | 63 | 54 |
| gtcta | tgtca | cttgt | aicat | acaga | 53 | 61 | 52 |
| gtcta | tgtca | cttgt | gaact | acaga | 54 | 63 | 54 |
| gtcta | tgtca | cttgt | cttgt | acaga | 54 | 63 | 54 |
| | | | Mean | | 53 | 61 | 53 |
| | | | Std Dev | | 1 | 1 | 1 |

Fig. 4E

SEQUENCE LISTING

<160> NUMBER OF SEQ ID NOS: 16

<210> SEQ ID NO 1
<211> LENGTH: 26
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: 10, 11, 12, 13, 14, 15, 16, 17
<223> OTHER INFORMATION: n = A,T,C or G

<400> SEQUENCE: 1
ggatcttctn nnnnnnnaga agcggg                                              26

<210> SEQ ID NO 2
<211> LENGTH: 11
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: 1, 2
<223> OTHER INFORMATION: n = A,T,C or G

<400> SEQUENCE: 2
nnagaagcgg g                                                              11

<210> SEQ ID NO 3
<211> LENGTH: 10
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: 1, 10
<223> OTHER INFORMATION: n = A,T,C or G

<400> SEQUENCE: 3 naccacacan                                                                10

<210> SEQ ID NO 4
<211> LENGTH: 25
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: 6, 7, 8, 9, 10, 11, 12, 13, 14, 15, 16, 17, 18, 19, 20
<223> OTHER INFORMATION: n = A,T,C or G

<400> SEQUENCE: 4
ggatcnnnnn nnnnnnnnnn gcggg                                               25

<210> SEQ ID NO 5
<211> LENGTH: 26
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: 2, 3, 4, 5, 6, 7, 8, 9, 10, 11, 17, 18, 19, 20, 21, 22,
      23, 24, 25
<223> OTHER INFORMATION: n = A,T,C or G

<400> SEQUENCE: 5
cnnnnnnnnn ngcatcnnnn nnnnna                                          26

<210> SEQ ID NO 6
<211> LENGTH: 65
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: 22
<223> OTHER INFORMATION: k is g or t
<220> FEATURE:
<221> NAME/KEY: misc_feature
<222> LOCATION: (23)...(31)
<223> OTHER INFORMATION: d is g, a, or t
<220> FEATURE:
<221> NAME/KEY: misc_feature
<222> LOCATION: 1, 2, 3, 4, 37, 38, 39, 40, 41, 42, 43, 44, 45, 46, 47,
      48, 49, 50, 51, 52, 53, 54, 55, 56, 63, 64, 65
<223> OTHER INFORMATION: n = A,T,C or G

<400> SEQUENCE: 6
nnnnggtacc gctcttcgtt gkdddddddd dgtcccnnnn nnnnnnnnnn nnnnnnaggc    60 ctnnn                                                                 65

<210> SEQ ID NO 7
<211> LENGTH: 29
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: 1, 2, 3, 10, 11, 12, 13, 14, 15, 16, 17, 18, 19, 20, 21,
      22, 23, 24
<223> OTHER INFORMATION: n = A,T,C or G

<400> SEQUENCE: 7
nnnaggcctn nnnnnnnnnn nnnngggac                                       29

<210> SEQ ID NO 8
<211> LENGTH: 42
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: 2, 3, 4, 5, 6, 7, 8, 9, 10, 11, 17, 18, 19, 20, 21, 22,
      23, 24, 25, 26, 27, 28, 29, 30, 31, 32, 33, 34, 35, 36, 37
<223> OTHER INFORMATION: n = A,T,C or G

<400> SEQUENCE: 8
cnnnnnnnnn ngcatcnnnn nnnnnnnnnn nnnnnnncat cc                        42

<210> SEQ ID NO 9
<211> LENGTH: 51
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: 10, 11, 12, 13, 14, 15, 16, 17, 18, 19, 20, 21, 22, 23,
      24, 25, 26, 27, 28, 29, 30, 31, 37, 38, 39, 40, 41, 42, 43, 44,
      45, 46
<223> OTHER INFORMATION: n = A,T,C or G -continued

<400> SEQUENCE: 9
gatcggatgn nnnnnnnnnn nnnnnnnnnn nctacgnnnn nnnnnngggc c    51

<210> SEQ ID NO 10
<211> LENGTH: 26
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: 7, 8, 9, 10, 11, 12, 13, 14, 15, 16, 17, 18, 19, 20, 21
<223> OTHER INFORMATION: n = A,T,C or G

<400> SEQUENCE: 10
aggcctnnnn nnnnnnnnnn ngggac    26

<210> SEQ ID NO 11
<211> LENGTH: 19
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: 6
<223> OTHER INFORMATION: k is g or t
<220> FEATURE:
<221> NAME/KEY: misc_feature
<222> LOCATION: (7)...(15)
<223> OTHER INFORMATION: d is g, a, or t

<400> SEQUENCE: 11
ccctgkdddd dddddgatc    19

<210> SEQ ID NO 12
<211> LENGTH: 40
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: 5
<223> OTHER INFORMATION: k is g or t
<220> FEATURE:
<221> NAME/KEY: misc_feature
<222> LOCATION: (6)...(14)
<223> OTHER INFORMATION: d is g, a, or t
<220> FEATURE:
<221> NAME/KEY: misc_feature
<222> LOCATION: 20, 21, 22, 23, 24, 25, 26, 27, 28, 29, 30, 31, 32, 33, 34
<223> OTHER INFORMATION: n = A,T,C or G

<400> SEQUENCE: 12
gatckddddd ddddgtcccn nnnnnnnnnn nnnnaggcct    40

<210> SEQ ID NO 13
<211> LENGTH: 40
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (27)...(35)
<223> OTHER INFORMATION: d is g, a, or t
<220> FEATURE:
<221> NAME/KEY: misc_feature
<222> LOCATION: 40

```
<223> OTHER INFORMATION: 5-methylcytosine
<220> FEATURE:
<221> NAME/KEY: misc_feature
<222> LOCATION: 7, 8, 9, 10, 11, 12, 13, 14, 15, 16, 17, 18, 19, 20, 21
<223> OTHER INFORMATION: n = A,T,C or G

<400> SEQUENCE: 13
aggcctnnnn nnnnnnnnnn ngggacdddd dddddkgatc                    40

<210> SEQ ID NO 14
<211> LENGTH: 19
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (4)...(4)
<223> OTHER INFORMATION: 5-methylcytosine
<220> FEATURE:
<221> NAME/KEY: misc_feature
<222> LOCATION: (5)...(13)
<223> OTHER INFORMATION: d is g, a, or t
<220> FEATURE:
<221> NAME/KEY: misc_feature
<222> LOCATION: 14
<223> OTHER INFORMATION: k is g or t
<220> FEATURE:
<221> NAME/KEY: misc_feature
<222> LOCATION: (17)...(19)
<223> OTHER INFORMATION: 5-methylcytosine

<400> SEQUENCE: 14
gatcdddddd dddkgtccc                                           19

<210> SEQ ID NO 15
<211> LENGTH: 19
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (6)...(14)
<223> OTHER INFORMATION: d is g, a, or t
<220> FEATURE:
<221> NAME/KEY: misc_feature
<222> LOCATION: 15
<223> OTHER INFORMATION: k is g or t

<400> SEQUENCE: 15
gggacddddd dddkgatc                                            19

<210> SEQ ID NO 16
<211> LENGTH: 27
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: 22
<223> OTHER INFORMATION: 5-methylcytosine
<220> FEATURE:
<221> NAME/KEY: misc_feature
<222> LOCATION: 1, 2, 3, 4, 5, 6, 7, 8, 9, 10, 11, 12, 13, 14, 15, 16,
      17, 18, 19, 20
<223> OTHER INFORMATION: n = A,T,C or G

<400> SEQUENCE: 16
nnnnnnnnnn nnnnnnnnnn gcatcag                                  27
```

METHODS AND COMPOSITIONS FOR TAGGING AND IDENTIFYING POLYNUCLEOTIDES

CROSS REFERENCE TO RELATED APPLICATIONS

This application is a Continuation of U.S. application Ser. No. 13/852,943, filed on Mar. 28, 2013, which application is a Continuation of U.S. application Ser. No. 13/466,894, filed on May 8, 2012, which application is a Continuation of U.S. application Ser. No. 13/425,215, filed on Mar. 20, 2012 (now U.S. Pat. No. 8,318,433), which is a Continuation of U.S. application Ser. No. 13/211,125, filed on Aug. 16, 2011 (now U.S. Pat. No. 8,168,385), which is a Continuation of U.S. application Ser. No. 12/111,043, filed on Apr. 28, 2008 (now U.S. Pat. No. 8,148,068), which is a Divisional of U.S. application Ser. No. 11/176,927, filed on Jul. 7, 2005 (now U.S. Pat. No. 7,393,665), which is a Continuation-In-Part of U.S. application Ser. No. 11/055,187, filed Feb. 10, 2005 (now U.S. Pat. No. 7,217,522), and claims benefit of U.S. Provisional App. No. 60/622,167, filed Mar. 16, 2005, the disclosures of which applications are incorporated in their entirety herein.

This application is a continuation-in-part of U.S. patent application Ser. No. 11/055,187 filed 10 Feb. 2005, which is incorporated by reference in its entirety; this application also claim priority form U.S. provisional patent application Ser. No. 60/662,167, filed 16 Mar. 2005, which is incorporated by reference in its entirety.

FIELD OF THE INVENTION

The present invention relates to methods and compositions for analyzing populations of polynucleotides, and more particularly, to methods and compositions for attaching oligonucleotide tags to polynucleotides and for identifying such polynucleotides by detection of the attached tag.

BACKGROUND

Oligonucleotide tags have frequently been employed to label and sort polynucleotides in analytical molecular biology, e.g. Brenner et al, Proc. Natl. Acad. Sci., 97: 1665-1670 (2000); Church et al, Science, 240: 185-188 (1988); Shoemaker et al, Nature Genetics, 14: 450-456 (1996); Hardenbol et al, Nature Biotechnology, 21: 673-678 (2003); and the like. The benefits of conducting analytical reactions with such molecular tags include (i) achievement of high degrees of multiplexing so that many analytes can be measured in the same reaction mixture with conservation of rare or expensive reagents, and (ii) ability to design oligonucleotide tags to optimize assay sensitivity, convenience, cost, and multiplexing capability. In most approaches, oligonucleotide tags are attached to polynucleotide analytes or probes in separate reactions, after which they are combined for multiplexed reactions, e.g. Church et al (cited above); Shoemaker et al (cited above); Hardenbol et al (cited above); Wallace, U.S. Pat. No. 5,981,176; and the like. Alternatively, unique oligonucleotide tags have also been attached to sets of polynucleotides in the same reaction by first forming a population of conjugates with a much larger set of oligonucleotide tags followed by removing a sample of polynucleotides (small in size relative to the oligonucleotide tag population), e.g. Brenner et al (cited above); Mao et al, International patent publication WO 02/097113. In the former approach, each analyte or probe may be identified in parallel by reading its oligonucleotide tag (whose sequence is known) in a single operation, e.g. by hybridization to a microarray. While such a readout is extremely efficient, the initial cost of synthesizing and separately labeling the analytes or probes is high. In the latter approach, the cost of attaching tags is low; however, the identity of the oligonucleotide tag attached to a given analyte or probe (even though unique) is unknown, so its use is limited to shuttling information about its probe or analyte to a readout platform.

It would be highly useful if a tagging method were available in which probes or analytes could each be uniquely labeled with an oligonucleotide tag in one or a few multiplex reactions employing a few tagging reagents, such that the resulting tags could be readily identified by a simple decoding procedure. Such a method would have the benefits both of the approach of separately attaching oligonucleotide tags (facile identification) and the approach of attaching oligonucleotide tags in multiplex reactions (less expense). Such a tagging method would find applications in many fields of scientific and biomedical research, particularly in genetics and cancer research where it is frequently necessary or desirable to analyze large numbers of polynucleotide analytes in rare or expensive samples.

SUMMARY OF THE INVENTION

The present invention provides a method and compositions for tagging polynucleotides and for identifying such tagged polynucleotides selected from a mixture. Oligonucleotide tags comprising a plurality of oligonucleotide subunits, or words, are attached to polynucleotides. Such tagged polynucleotides are then assayed in parallel, where one or more tagged polynucleotides may be selected, for example, those having particular single nucleotide polymorphisms at one or more loci. The polynucleotides selected in the assay are then identified by analyzing their respective tags in accordance with the invention.

In one aspect, words of oligonucleotide tags index mixtures in successively more complex sets of mixtures (or "tiers" of mixtures, as described more fully below) that a polynucleotide goes through in the tagging method of the invention. By identifying each word of an oligonucleotide tag, a sequence of submixtures is identified including the very first submixture that contains only a single polynucleotide, thereby providing the identity of the selected polynucleotide. The analysis of the words of an oligonucleotide tag can be carried out in parallel, e.g. by specific hybridization of the oligonucleotide tag to its tag complement on an addressable array; or such analysis may be carried out serially by successive specific hybridizations of labeled word complements, or by other serial processes described more fully below.

In one aspect, the invention provides a method of generating a mixture of genomic fragments from a plurality of individuals wherein each fragment from a different individual has a different oligonucleotide tag attached. Preferably, in this aspect, fragments from the same individual have the same oligonucleotide tag attached. That is, each individual is associated with a single unique oligonucleotide tag. In one aspect, such method of generating a mixture of tagged polynucleotides is carried out with the following steps: (a) providing a mutually discriminable set containing a plurality of words; (b) separately attaching a different word to each of a plurality of different polynucleotides to form tag-polynucleotide conjugates, the plurality of different polynucleotides being equal to or less than the plurality of words; (c) repeating step (b) for each of the plurality of words to form a base tier of submixtures and recording which word is attached to each polynucleotide in each submixture; (d) combining tag-polynucleotide conjugates to form a tier of submixtures wherein each different polynucleotide within a submixture has an oligonucleotide tag that is different from that of any other polynucleotide in the same submixture; (e) adding a different word to each different submixture of step (d) to form another tier of submixtures of tag-polynucleotide conjugates and recording which word is attached to each tag-polynucleotide conjugate in each submixture; and (f) repeating steps (d) and (e) until each polynucleotide has an oligonucleotide tag attached.

In another aspect of the invention, polynucleotides, such as DNA fragments from different genomes, are tagged with different oligonucleotide tags that are concatenates of a plurality of oligonucleotide subunits, wherein the subunits of the oligonucleoitde tag identify in a position-dependent manner successively less complex sub-mixtures from which the DNA fragments were derived. In one embodiment of this aspect, a polynucleotide is identified in a mixture of such tagged polynucleotide by the following steps: (a) selecting a tagged polynucleotide from a mixture of tagged polynucleotides assembled from one or more tiers of submixtures, at least one such tier being a base tier containing submixtures that each contain a single polynucleotide of known identity, each tagged polynucleotide of the mixture comprising a polynucleotide attached to a concatenate of oligonucleotide subunits such that each different polynucleotide has a different concatenate and each oligonucleotide subunit has a nucleotide sequence and a position within such concatenate, the position of the oligonucleotide subunit uniquely identifying a tier of submixtures and the nucleotide sequence of the oligonucleotide subunit uniquely identifying a submixture within such tier of submixtures; and (b) determining the nucleotide sequence of each oligonucleotide subunit at each position of the concatenate of the tagged polynucleotide to determine a submixture within the base tier containing the polynucleotide, thereby determining the identity of the polynucleotide.

In another aspect of the invention, compositions comprising sets of oligonucleotide tags are provided that may be identified by successively identifying words by specific hybridization of word complements. In one embodiment of this aspect, such sets comprise a plurality of oligonucleotides each having a length of at least eight nucleotides and each comprising a concatenate of two or more subunits, wherein each subunit has a length of from 3 to 10 nucleotides and is selected from the same mutually discriminable set, and wherein each subunit within a concatenate is different.

In certain embodiments, after a sub-population is selected, the members of the subpopulation may be simultaneously analyzed using the unique tags on the polynucleotides. In one aspect, such sorting of uniquely tagged polynucleotides allows massively parallel operations, such as simultaneously sequencing many thousands of genomic DNA fragments from different genomes. The sequence contains sufficient information to identify the source of a polynucleotide in a population. The isolated fragments in the reaction mixture may be analyzed by a variety of techniques to identify SNPs or haplotypes.

DEFINITIONS

Figure 1A:
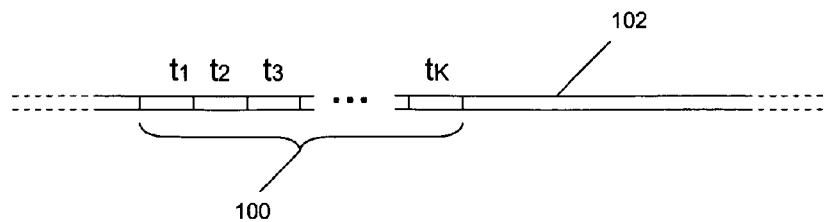
FIGS. 1A-1B illustrate an oligonucleotide tag-polynucleotide conjugate wherein the oligonucleotide tag is a concatenate of a plurality of words.

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Addressable" in reference to tag complements means that the nucleotide sequence, or perhaps other physical or chemical characteristics, of an end-attached probe, such as a tag complement, can be determined from its address, i.e. a one-to-one correspondence between the sequence or other property of the end-attached probe and a spatial location on, or characteristic of, the solid phase support to which it is attached. Preferably, an address of a tag complement is a spatial location, e.g. the planar coordinates of a particular region containing copies of the end-attached probe. However, end-attached probes may be addressed in other ways too, e.g. by microparticle size, shape, color, frequency of micro-transponder, or the like, e.g. Chandler et al, PCT publication WO 97/14028.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g.

"real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Complementary or substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

"Complexity" in reference to a nucleic acid sequence means the total length of unique sequence in one or more polynucleotides, such as polynucleotides in a population, e.g. a cDNA or genomic library, or in a genome. The complexity of a genome can be equivalent to or less than the length of a single copy of the genome (i.e. the haploid sequence). The concept of nucleic acid complexity and its affect on assays is further disclosed in the following references: Wetmur, Critical Reviews in Biochemistry and Molecular Biology, 26: 227-259 (1991); Britten and Davidson, chapter 1 in Hames et al, editors, Nucleic Acid Hybridization: A Practical Approach (IRL Press, Oxford, 1985).

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick basepairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Genetic locus," or "locus" in reference to a genome or target polynucleotide, means a contiguous subregion or segment of the genome or target polynucleotide. As used herein, genetic locus, or locus, may refer to the position of a nucleotide, a gene, or a portion of a gene in a genome, including mitochondrial DNA, or it may refer to any contiguous portion of genomic sequence whether or not it is within, or associated with, a gene. In one aspect, a genetic locus refers to any portion of genomic sequence, including mitochondrial DNA, from a single nucleotide to a segment of few hundred nucleotides, e.g. 100-300, in length.

"Genetic variant" means a substitution, inversion, insertion, or deletion of one or more nucleotides at genetic locus, or a translocation of DNA from one genetic locus to another genetic locus. In one aspect, genetic variant means an alternative nucleotide sequence at a genetic locus that may be present in a population of individuals and that includes nucleotide substitutions, insertions, and deletions with respect to other members of the population. In another aspect, insertions or deletions at a genetic locus comprises the addition or the absence of from 1 to 10 nucleotides at such locus, in comparison with the same locus in another individual of a population.

"Kit" refers to any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213.

"Microarray" refers to a solid phase support having a planar surface, which carries an array of nucleic acids, each member of the array comprising identical copies of an oligonucleotide or polynucleotide immobilized to a spatially defined region or site, which does not overlap with those of other members of the array; that is, the regions or sites are spatially discrete. Spatially defined hybridization sites may additionally be "addressable" in that its location and the identity of its immobilized oligonucleotide are known or predetermined, for example, prior to its use. Typically, the oligonucleotides or polynucleotides are single stranded and are covalently attached to the solid phase support, usually by a 5'-end or a 3'-end. The density of non-overlapping regions containing nucleic acids in a microarray is typically greater than 100 per $cm^2$, and more preferably, greater than 1000 per $cm^2$. Microarray technology is reviewed in the following references: Schena, Editor, Microarrays: A Practical Approach (IRL Press, Oxford, 2000); Southern, Current Opin. Chem. Biol., 2: 404-410 (1998); Nature Genetics Supplement, 21: 1-60 (1999). As used herein, "random microarray" refers to a microarray whose spatially discrete regions of oligonucleotides or polynucleotides are not spatially addressed. That is, the identity of the attached oligonucleoties or polynucleotides is not discernable, at least initially, from its location. In one aspect, random microarrays are planar arrays of microbeads wherein each microbead has attached a single kind of hybridization tag complement, such as from a minimally cross-hybridizing set of oligonucleotides. Arrays of microbeads may be formed in a variety of ways, e.g. Brenner et al, Nature Biotechnology, 18: 630-634 (2000); Tulley et al, U.S. Pat. No. 6,133,043; Stuelpnagel et al, U.S. Pat. No. 6,396,995; Chee et al, U.S. Pat. No. 6,544,732; and the like. Likewise, after formation, microbeads, or oligonucleotides thereof, in a random array may be identified in a variety of ways, including by optical labels, e.g. fluorescent dye ratios or quantum dots, shape, sequence analysis, or the like.

"Nucleoside" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6: 855-870 (1996); Mesmaeker et al, Current Opinion in Structural Biology, 5: 343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

"Oligonucleotide tag" means an oligonucleotide that is attached to a polynucleotide and is used to identify and/or track the polynucleotide in a reaction. Usually, a oligonucleotide tag is attached to the 3'- or 5'-end of a polynucleotide to form a linear conjugate, sometime referred to herein as a "tagged polynucleotide," or equivalently, an "oligonucleotide tag-polynucleotide conjugate," or "tag-polynucleotide conjugate." Oligonucleotide tags may vary widely in size and compositions; the following references provide guidance for selecting sets of oligonucleotide tags appropriate for particular embodiments: Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In different applications of the invention, oligonucleotide tags can each have a length within a range of from 4 to 36 nucleotides, or from 6 to 30 nucleotides, or from 8 to 20 nucleotides, respectively. In one aspect, oligonucleotide tags are used in sets, or repertoires, wherein each oligonucleotide tag of the set has a unique nucleotide sequence. In some embodiment, particularly where oligonucleotide tags are used to sort polynucleotides, or where they are identified by specific hybridization, each oligonucleotide tag of such a set has a melting temperature that is substantially the same as that of every other member of the same set. In such aspects, the melting temperatures of oligonucleotide tags within a set are within 10° C. of one another; in another embodiment, they are within 5° C. of one another; and in another embodiment, they are within 2° C. of one another. In another aspect, oligonucleotide tags are members of a mutually discriminable set, as described more fully below. The size of mutually discriminable sets of oligonucleotide tags may vary widely. Such a set of oligonucleotide tags may have a size in the range of from several tens to many thousands, or even millions, e.g. 50 to $1.6 \times 10^6$. In another embodiment, such a size is in the range of from 200 to 40,000; or from 1000 to 40,000; or from 1000 to 10,000. In another aspect of the invention, oligonucletide tags comprise a concatenation of subunits, such as described by Brenner et al, Proc. Natl. Acad. Sci., 97: 1665-1670 (2000). In such concatenates, oligonucleotide subunits, or words, can be selected from a set of subunits with the properties of mutual discriminability and substantially equivalent melting temperature. Constructing oligonucleotide tags from a plurality of oligonucleotide subunits permits the convenient and inexpensive formation of very large sets of oligonucleotide tags, e.g. as described by Brenner et al, Proc. Natl. Acad. Sci., 97: 1665-1670 (2000). Also, the use of oligonucleotide subunits permits enzymatic synthesis and/or attachment of oligonucleotide tags to polynucleotides, e.g. as described below and in Brenner and Williams, U.S. patent publication 2003/0049616. In one aspect, oligonucleotide tags comprise a plurality of oligonucleotide subunits. Such subunits may vary widely in length. In one aspect, the length of oligonucleotide subunits is in the range of from 2 to 18 nucleotides; in another aspect, the length of oligonucleotide subunits is in the range of from 2 to 8 nucleotides; and in another aspect the length of oligonucleotide subunits is in the range of from 2 to 5 nucleotides. A plurality of oligonucleotide subunits making up an oligonucleotide tag may also vary widely depending on their application. In one aspect, such plurality is a number in the range of 2 to 10; and in another aspect, such plurality is a number in the range of from 2 to 6. The size of a set of oligonucleotide subunits is usually smaller than the size of a set of oligonucleotide tags. Usually, a set of oligonucleotide subunits has a size in the range of from 2 to 20; or in another embodiment, from 2 to 10; or in another embodiment, from 4 to 8. It is clear to one of ordinary skill that for subunits only two nucleotides in length that the size of a set of subunits would be smaller than that of subunits having greater lengths.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature>90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred µL, e.g. 200 µL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999)(two-color real-time PCR). Usually, distinct sets of primers are employed for each sequence being amplified. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, β$_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Polynucleotide" or "oligonucleotide" are used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moities, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 14 to 36 nucleotides.

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the address and fluorescence intensity of a signal being generated at each hybridization site of the microarray; thus, such a readout may be registered or stored in various ways, for example, as an image of the microarray, as a table of numbers, or the like.

"Solid support", "support", and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Microarrays usually comprise at least one planar solid phase support, such as a glass microscope slide.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

"$T_m$" or "melting temperature" is the temperature at which a population of double-stranded nucleic acid molecules becomes half dissociated into single strands. Several equations for calculating the Tm of nucleic acids are well known in the art. As indicated by standard references, a simple estimate of the Tm value may be calculated by the equation. $Tm=81.5+0.41 (\% G+C)$, when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr., Biochemistry 36, 10581-94 (1997)) include alternative methods of computation which take structural and environmental, as well as sequence characteristics into account for the calculation of Tm.

"Sample" means a quantity of material from a biological, environmental, medical, or patient source in which detection or measurement of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

"Sequence determination" or "determining a nucleotide sequence" in reference to polynucleotides includes determination of partial as well as full sequence information of the polynucleotide. That is, the term includes sequence comparisons, fingerprinting, and like levels of information about a target polynucleotide, as well as the express identification and ordering of nucleosides, usually each nucleoside, in a target polynucleotide. The term also includes the determination of the identity, ordering, and locations of one, two, or three of the four types of nucleotides within a target polynucleotide. For example, in some embodiments sequence determination may be effected by identifying the ordering and locations of a single type of nucleotide, e.g. cytosines, within the target polynucleotide "CATCGC . . . " so that its sequence is represented as a binary code, e.g. "100101. . . " for "C-(not C)-(not C)-C-(not C)-C . . . " and the like.

DETAILED DESCRIPTION OF THE INVENTION

The invention provides methods and compositions for attaching oligonucleotide tags to polynucleotides for the purpose of carrying out analytical assays in parallel and for decoding the oligonucleotide tags of polynucleotides selected in such assays. Exemplary analytical assays where tagged polynucleotides are selected include genotyping assays, such as disclosed in the following references that are incorporated by references: Brenner, PCT patent publication WO 2005/026686; Willis et al, U.S. Pat. No. 6,858,412; Fan et al, U.S. patent publication 2005/0074787; Schouten, U.S. patent publication 2003/0108913; and the like. Selection of a tagged polynucleotide may be based on specific hybridization and differential duplex stability, template-driven ligation, template-driven strand extension, exonuclease digestion (e.g. of non-circularized probes), or the like.

Figure 1B:
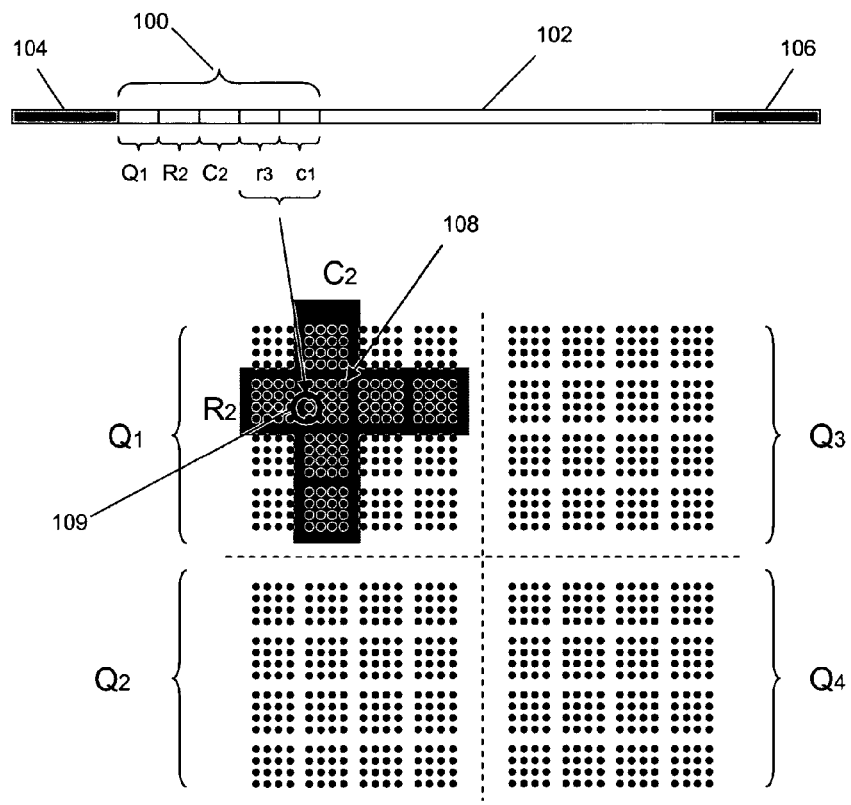

In one aspect, as illustrated in FIG. 1A, oligonucleotide tags (100) of the invention are concatenates of a plurality of oligonucleotide subunits, or words (e.g., labeled $t_1, t_2, t_3, \ldots t_k$ in FIG. 1A) that can be attached to polynucleotide (102) to form a linear conjugate. In another aspect of the invention, words are added to polynucleotides in a succession of mixtures, each one more complex than the previous one. (Thus, in the embodiment illustrated below, each added word provides an address of a successively more complex submixture, in analogy to a geographical progression: house, street, district, city, state, country, and so on). That is, as illustrated in FIG. 1B, where each dot represents a vessel or well (e.g. in a 384-well plate, or like apparatus) containing a single kind of polynucleotide, each different kind of polynucleotide in each 4×4 subgroup has a different two words pair attached that provide a unique address for each polynucleotide in the 4×4 subgroup. In this example, such addresses are provided by words from a mutually discriminable set of words having at least four members. For larger starting subgroups, e.g. 8×8 as disclosed below, larger sets of words are required. Thus, in FIG. 1B, words $r_3$ and $c_1$ give the address of polynucleotide (102) within subgroup (108), the location being indicated by circle (109). Words $C_2$ and $R_2$ give the address of subgroup (108) within a quadrant, and word $Q_1$ indicates the quadrant in which subgroup (108) is located. In certain embodiments and as discussed below, tagged polynucleotides may have one or more adaptors attached (104) and (106) which facilitate certain polynucleotide tagging and/or manipulation steps.

Figure 2A:
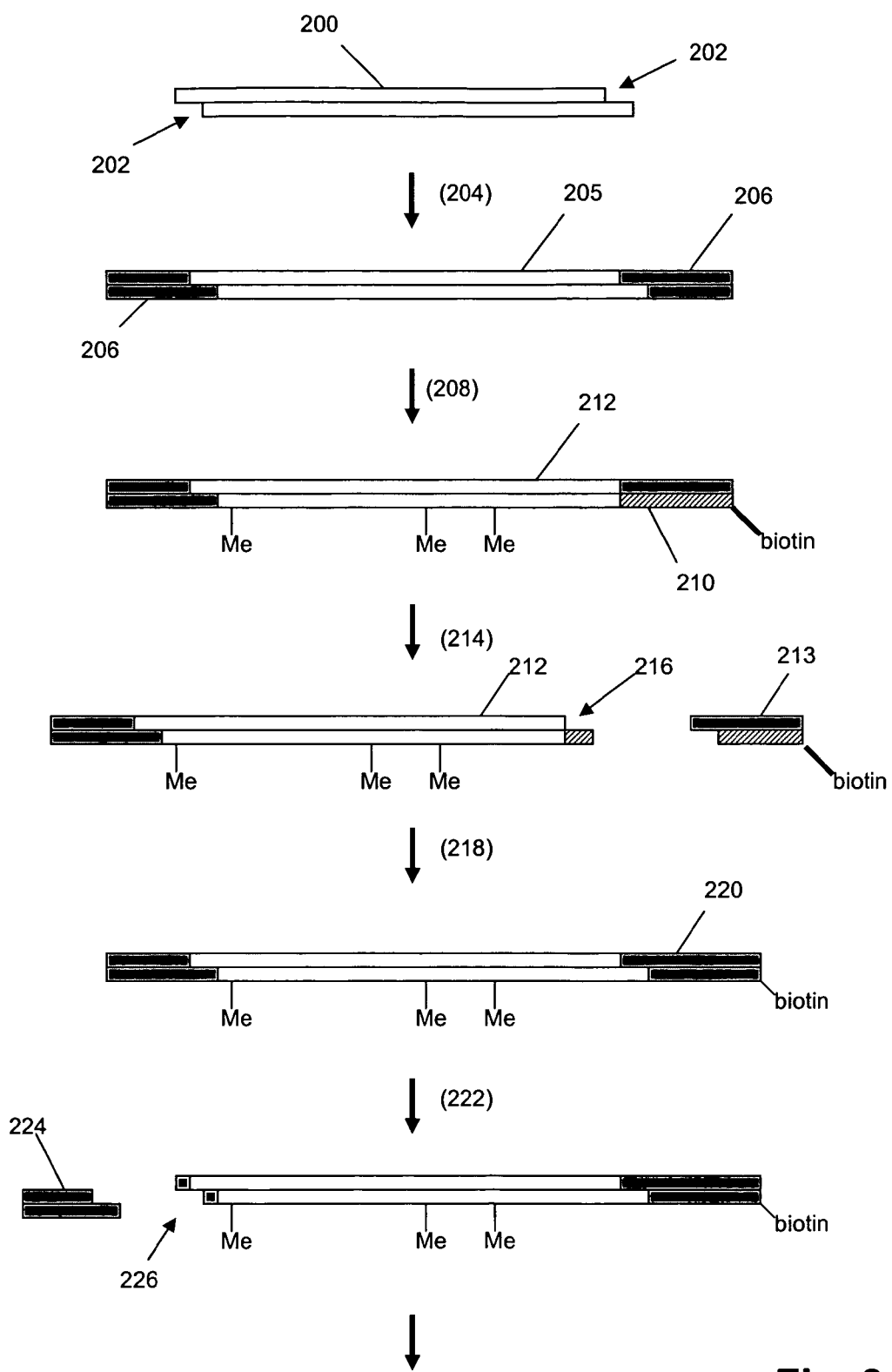
FIGS. 2A-2B illustrate a procedure for attaching an oligonucleotide tag to a polynucleotide by attaching words one at a time.
Figure 2B:
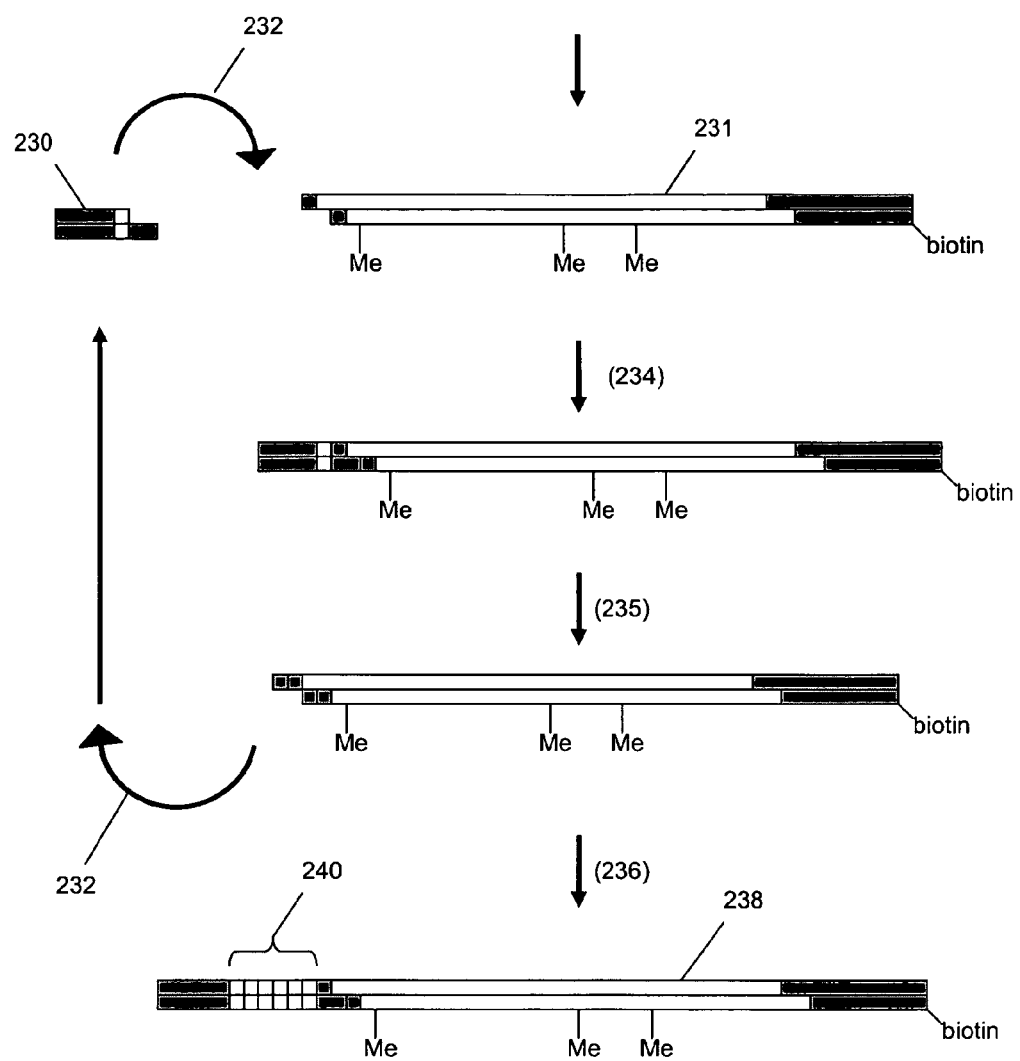

A method of attaching oligonucleotide tags of the invention to polynucleotides is illustrated in FIGS. 2A-2B. Polynucleotides (200) are generated that have overhanging ends (202), for example, by digesting a sample, such as genomic DNA, cDNA, or the like, with a restriction endonuclease. Preferably, a restriction endonuclease is used that leaves a four-base 5' overhang that can be filled-in by one nucleotide to render the fragments incapable of self-ligation. For example, digestion with Bgl II followed by an extension with a DNA polymerase in the presence of dGTP produces such ends. Next, to such fragments, single-word adaptors (206) are ligated (204). Single-word adaptors (206) (i) attach a first word of an oligonucleotide tag to both ends of each fragment (200). Single-word adaptors (206) also contain a recognition site for a type IIs restriction endonuclease that preferably leaves a 5' four base overhang and that is positioned so that its cleavage site corresponds to the position of the newly added word, as described more fully in the examples below. (Such cleavage allows words to be added one-by-one by use of a set of adaptors containind word pairs, or "di-words," described more fully below). In one aspect, a single-word adaptor (206) is separately ligated to fragments (200) from each different individual genome.

In order to carry out enzymatic operations at only one end of adaptored fragments (205), one of the two ends of each fragment is protected by methylation and operations are carried out with enzymes sensitive to 5-methyldeoxycytidine in their recognition sites. Adaptored fragments (205) are melted (208) after which primer (210) is annealed as shown and extended by a DNA polymerase in the presence of 5-methyldeoxycytidine triphosphate and the other dNTPs to give hemi-methylated polynucleotide (212). Polynucleotides (212) are then digested (214) with a restriction endonuclease that is blocked by a methylated recognition site, e.g. Dpn II (which cleaves at a recognition site internal to the Bgl II site and leaves the same overhang). Accordingly, such restriction endonucleases must have a deoxycytidine in its recognition sequence and leave an overhanging end to facilitate the subsequent ligation of adaptors. Digestion leaves fragment (212) with overhang (216) at only one end and free biotinylated fragments (213). After removal (218) of biotinylated fragments (213) (for example by affinity capture with avidinated beads), adaptor (220) may be ligated to fragment (212) in order to introduce sequence elements, such as primer binding sites, for an analytical operation, such as sequencing, SNP detection, or the like. Such adaptor is conveniently biotinylated for capture onto a solid phase support so that repeated cycles of ligation, cleavage, and washing can be implemented for attaching words of the oligonucleotide tags. After ligation of adaptor (220), a portion of single-word adaptor (224) is cleaved (222) so that overhang (226) is created that includes all (or substantially all, e.g. 4 out of 5 bases of) the single word added by single-word adaptor (206). After washing to remove fragment (224), a plurality of cycles (232) are carried out in which adaptors (230) containing di-words are successively ligated (234) to fragment (231) and cleaved (235) to leave an additional word. Such cycles are continued until the oligonucleotide tags (240) are complete (236), after which the tagged polynucleotides (238) may be subjected to analysis directly, or single strands thereof may be melted from the solid phase support for analysis.

Non-Sequential Decoding

In some tagging schemes, words may be repeated within an oligonucleotide tag. For example, where all words are selected from the same mutually discriminable set "with replacement" (i.e. at each word position within a concatenate, any word of a set can be added), then repeated words are possible. In such embodiments, oligonucleotide tags can be decoded (that is, its associated polynucleotide can be identified) in a number of ways. In one aspect, labeled copies of oligonucleotide tags can be specifically hybridized to their tag complements on an addressable microarray, or like read-out platform. Alternatively, particularly in the case of ligation tags, the oligonucleotide tags can be translated into a different kind of tag that permits a particular type of readout. For example, ligation tags can be specifically hybridized directly to a microarray of tag complements (preferably, comprising oligonucleotide analogs such as PNAs that have enhanced binding energy per basepair) or ligation tags can be specifically hybridized indirectly to a microarray of tag complements by first translating them into a hybridization tags of greater length. Ligation tags also can be translated into size-coded tags that can be identified by separating by electrophoresis. The former decoding is carried out using the tag translation methods disclosed in Brenner, PCT patent publication WO 2005/026686, which is incorporated herein by reference. The latter decoding is carried out using the tag translation method disclosed in Brenner, U.S. provisional patent Ser. No. 60/662,167, which is incorporated herein by reference.

Sequential Decoding

Figure 3A:
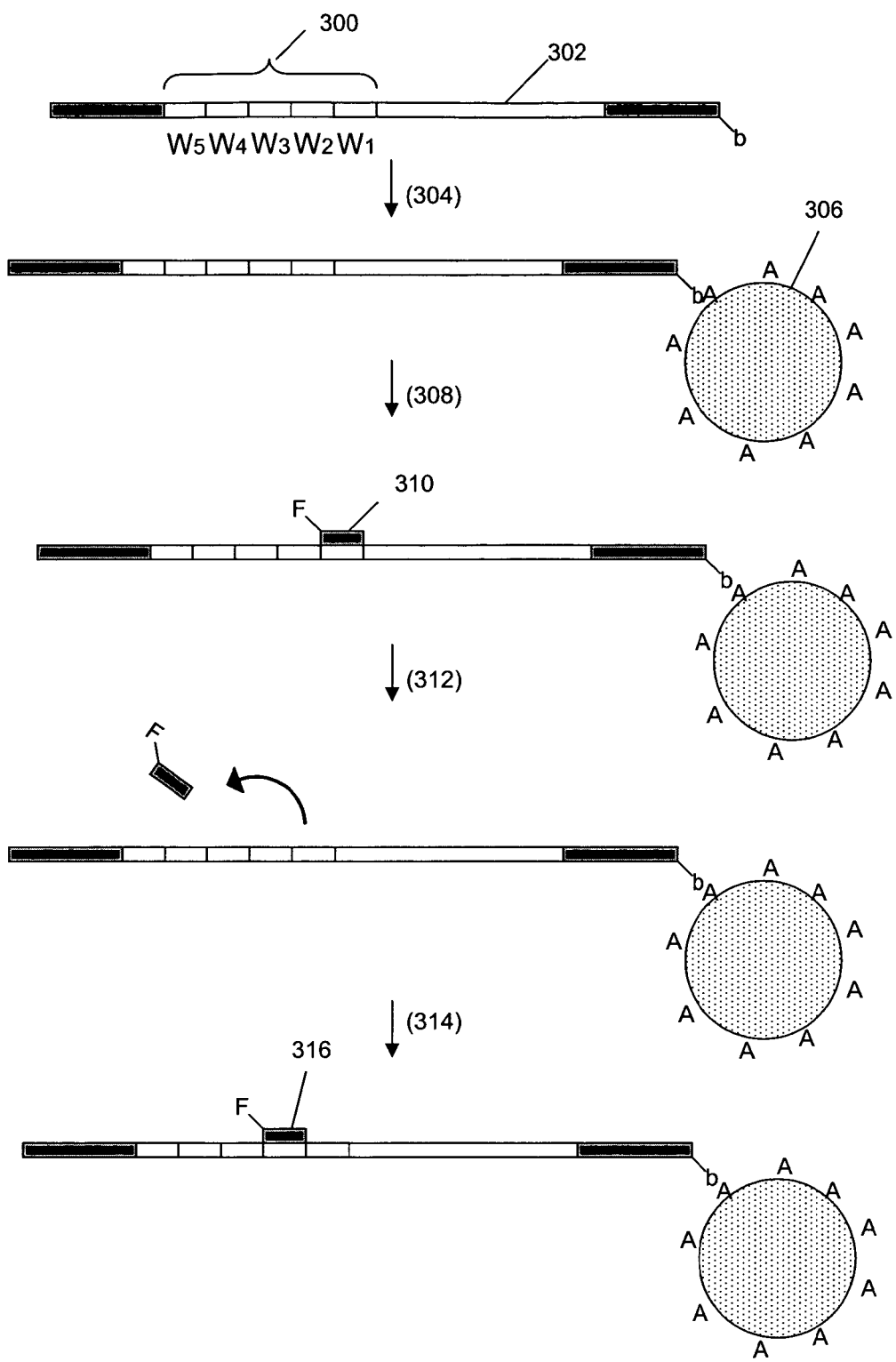
FIGS. 3A-3B illustrate a procedure for decoding an oligonucleotide tag by successively hybridizing labeled word complements.
Figure 3B:
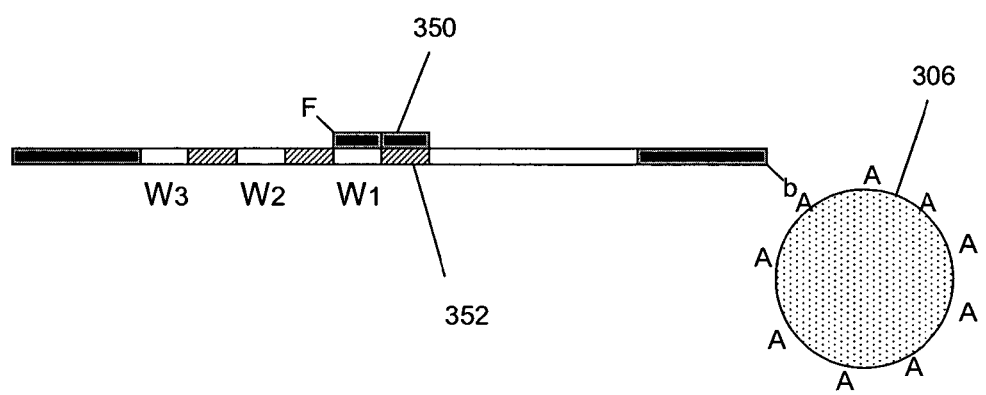

In tagging schemes where there are no repeated words in an oligonucleotide tag (as disclosed below), in addition to parallel decoding, such as specific hybridization of the entire oligonucleotide tags to their respective tag complements, such oligonucleotide tags can be decoded sequentially by word-by-word identification. As illustrated in FIG. 3A, tagged polynucleotide (302) has oligonucleotide tag (300) that does not contain repeated words. Such polynucleotide is captured (304) onto a solid phase support (306), using conventional protocols, e.g. avidin or streptavidin capture via a biotin moiety. Labeled anti-word (310) is then specifically hybridized to its corresponding word in the oligonucleotide tag (308) and detected via a fluorescent label, or like label, after which it is melted (312) and the next anti-word (316) is specifically hybridized (314). The process is repeated until all of the words are identified. In some embodiments, as illustrated in FIG. 3B, anti-words (350) may include a segment that is complementary to a spacer segment (352) adjacent and between words, e.g. $W_1$, $W_2$, and $W_3$.

Ligation Tags

In one aspect, oligonucleotides of the invention include tags that achieve discrimination both by sequence differences and by ligation. These are referred to herein as "ligation tags." In one aspect, ends of ligation tags are correlated in that if one end matches, which is required for ligation, the other end matches as well. The sequences also allow the use of a special set of enzymes which can create overhangs of (for example) eight bases required for a set of 4096 different sequences. In one aspect, ligation tags of a set each have a length in the range of from 6 to 12 nucleotides, and more preferably, from 8 to 10 nucleotides. In one aspect, a set of ligation tags is selected so that each member of a set differs from every other member of the same set by at least one nucleotide. In the following disclosure, it is assume that a starting DNA is obtainable having the following form:

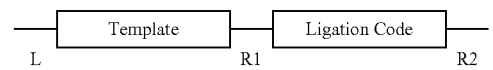

where L is a sequence to the "left" of the template that may be preselected, and R1 and R2 are primer binding sites (to the "right" of the template) In one aspect, nucleotide sequences of ligation tags in a set, i.e. ligation codes, may be defined by the following formula:

where Y is A, C, G, or T; N is any nucleotide; and Z is (5'→3') GT, TG, CA, or AC. The central doublet, Z, is there there so that restriction enzymes can be used to create the overhangs. Note ends of the tags are correlated, so if one does not ligate, the other will not either. Thus, the ends and the middle pair differ by 2 bases out of 8 from nearest neighbors, i.e. 25%, whereas the inners differ by one base in 8, i.e. 12.5%. Note that the above code may be expanded to give over 16,000 tags by adding an additional doublet, as in the formula: 5'-Y[NN]ZZ[NN]Y, where each Z is independently selected from the set of doublets.

In order to create an overhang of bases, a combination of a nicking enzyme and a type IIs restriction endonuclease having a cleavage site outside of its recognition site is used. Preferably, such type I is restriction endonuclease leaves a 5' overhang. Such enzymes are selected along with the set of doublets, Z, to exclude such sites from the ligation code. In one aspect, the following enzymes may be used with the above code: Nicking enzyme: N.Alw I (GGATCN$_4$↓); Restriction enzyme: Fau I (CCCGC(N$_4$/N$_6$)). Sap I (GCTCTTC(N$_1$/N$_4$)) may also be used as a restriction enzyme. In one example, these enzymes are used with the following segments:

| Enzyme | Sequence |
| --- | --- |
| N.Alw I | GGATC[TTCT]↓ |
| Fau I | CCCGC[TTCT]↓ |
| Sap I | GCTCTTC[T]↓ |

A 5' overhang can be created as follows, if a ligation code, designated as "[LIG8]," is present (SEQ ID NO: 1):

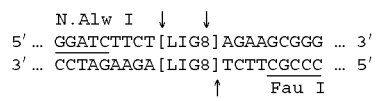

When this structure is cleaved as shown above, two double-stranded pieces are formed (SEQ ID NO: 2):

where "p" represents a phosphate group.

As described above, the doublet code, Z, consisted of TG, GT, AC, and CA. These differ from each other by two mismatches and a 5 word sequence providing 1000 different sequences has a discrimination of 2 bases in 10. Another way to consider such a doublet structure is to define symbols c=C or G, a=A or T. The above code can then be expressed as ca, aa, cc, and ac. ca has the dinucleotides CA, CT, GA, and GT. Notice that in this set, each "word" differs by 1 mismatch from 2 members of the set but by 2 mismatches from the remaining members. The doublet code is present by definition. In fact, it is easy to see that if another repeat structure is selected, for example, caca, then many words would be found that differ by two mismatches. The c and a pairs may be arranged in any manner. For example, a sequence defining a set of 256 members could be, cacacaca, which has a clearly defined substructure, or acaaccca, which has no repeated segments. Both have 50% GC and neither has sequences that are self complementary, but the following sequence does: cacaacac.

It is well known that the melting and annealing behavior of DNA sequences depends not only on the amount GC, but more strongly on the neighboring base. Thus, cc pairs GG, CC, CG, GC contribute most to duplex stability, while ca and ac pairs make the same but lower contribution and, of the aa pairs TA is lower than the remaining three AT, AA and TT, which are like the ca and ac set. The weakness of the doublet code is that the junctions between the doublets generate cases where there are GG in one sequence and TA in another at the same place. This cannot happen with the binary code chosen above no matter how the units are arranged. Thus, cc would be uniformly high and the aa low but with the pair TA being lower than the others. Another binary system, e.g. t=G or T, s=C or A, would have a different neighbor structure in which there would be GC and TA at the same place.

It is desirable that this criterion be extended to the neighbors of the outer correlated nucleotides, which can be accomplished by requiring a sequence that begins with an a and ends with an a. A code for the inner 8 bases which satisfies these conditions is the following (SEQ ID NO: 3):

5'-Y'accacacaY"

where Y' is G, A, T, or C, and Y" is T whenever Y' is G, C whenever Y' is A, G whenever Y' is T, and A whenever Y' is C.

Direct Readout of Ligation Tags

In one aspect, after an analytical operation is conducted in which tags are selected and labeled, such tags may be detected on an array, or microarray, of tag complements, as shown below. Selected ligation tags may be in an amplifiable segment as follows (SEQ ID NO: 4):

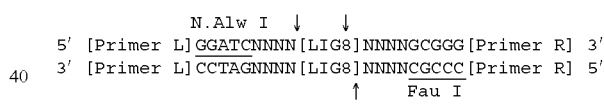

Cleavage of this structure gives the following, the upper strand of which may be labeled, e.g. with a fluorescent dye, quantum dot, hapten, or the like, using conventional techniques:

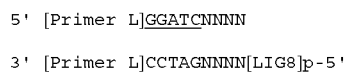

This fragment may be hybridized to an array of tag complements such as the following:

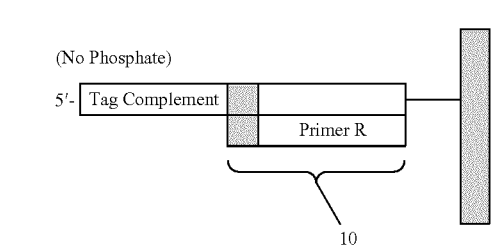

where the oligonucleotide designated as "10" may be added before or with the labeled ligation tag.

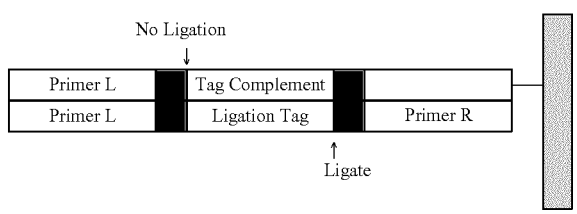

After a hybridization reaction, hybridized ligation tags are ligated to oligonucleotide "10" to ensure that a stable structure is formed. The ends between the upper Primer L and the tag complement are not ligated because of the absence of a 5' phosphate on the tag complement. Such an arrangement permits the washing and re-use of the solid phase support. In one aspect, tag complements and the other components attached to the solid phase support are peptide nucleic acids (PNAs) to facilitate such re-use.

Hybridization Tags

A feature of the invention is the use of oligonucleotide tags to uniquely label members of a population of polynucleotides. A wide variety of oligonucleotide tags may be employed for this purpose. In one aspect, oligonucleotide tags are selected from the same set of oligonucleotides that have nucleotide sequences that render them mutually discriminable. That is, annealing conditions, or hybridization conditions, are available so that an oligonucleotide tag of a set forms a stable duplex with essentially only its complement and not with the complements of any other oligonucleotide tag of the same set. A set of mutually discriminable oligonucleotide tags can vary widely in sequence, length, and internal structure. In one aspect, each oligonucleotide tag of such a set differs in sequence from every other member of the same set in at least ten percent of its nucleotide positions or each is selected from a minimally cross-hybridizing set of oligonucleotides. In another aspect, each oligonucleotide tag of such a set differs in sequence from every other member of the same set in at least fifteen percent of its nucleotide positions or each is selected from a minimally cross-hybridizing set of oligonucleotides. Thus, in the latter example, a set of 6-mer oligonucleotides whose members each differ from one another by at least one nucleotide form a mutually discriminable set.

In another aspect, mutually discriminable oligonucleotide tags are selected solely from a minimally cross-hybridizing set of oligonucleotides, or assembled from oligonucleotide subunits, i.e. "words," selected from a minimally cross-hybridizing set of oligonucleotides. Construction of such minimally cross-hybridizing sets are disclosed in Brenner et al, U.S. Pat. No. 5,846,719; Brenner et al, Proc. Natl. Acad. Sci., 97: 1665-1670 (2000); and Brenner and Williams, U.S. patent publication 2003/0049616, which references are incorporated by reference. In accordance with Brenner, the sequences of oligonucleotides of a minimally cross-hybridizing set differ from the sequences of every other member of the same set by at least two nucleotides. Thus, each member of such a set cannot form a duplex (or triplex) with the complement of any other member with less than two mismatches. Preferably, perfectly matched duplexes of tags and tag complements of either the same mutually discriminable set or the same minimally cross-hybridizing set have approximately the same stability, especially as measured by melting temperature and/or dissociation temperature. Complements of hybridization tags, referred to herein as "tag complements," may comprise natural nucleotides or non-natural nucleotide analogs. Hybridization tags when used with their corresponding tag complements provide a means of enhancing the specificity, or discrimination, of hybridization.

Minimally cross-hybridizing sets of oligonucleotide tags and tag complements may be synthesized either combinatorially or individually depending on the size of the set desired and the degree to which cross-hybridization is sought to be minimized (or stated another way, the degree to which specificity is sought to be enhanced). For example, a minimally cross-hybridizing set may consist of a set of individually synthesized 10-mer sequences that differ from each other by at least 4 nucleotides, such set having a maximum size of 332, when constructed as disclosed in Brenner et al, International patent application PCT/US96/09513. Alternatively, a minimally cross-hybridizing set of oligonucleotide tags may also be assembled combinatorially from subunits which themselves are selected from a minimally cross-hybridizing set. For example, a set of minimally cross-hybridizing 12-mers differing from one another by at least three nucleotides may be synthesized by assembling 3 subunits selected from a set of minimally cross-hybridizing 4-mers that each differ from one another by three nucleotides. Such an embodiment gives a maximally sized set of $9^3$, or 729, 12-mers.

Comma-less Hybridization Tags

In one aspect of the invention, oligonucleotide tags are hybridized to their complementary sequences, or "anti-tags," which are attached to a solid phase support, such as a microarray. In such circumstances, it is desirable to employ oligonucleotide tags that are highly specific for anti-tags that form perfectly matched duplexes between each and every word of the tag, and that form, at best, only weakly stable duplexes with anti-tags in which words are not perfectly aligned. That is, in order to avoid spurious signals, it is desirable select sets of words (and tags constructed from them) that do not form stable duplexes when hybridized in an imperfectly aligned configuration, e.g. shifted 1 to 2, or more, bases out of perfect alignment. Sets of words with such properties may be constructed in several ways, including by inserting "commas" between words or by using words that inherently possess the above properties, i.e. which result in so-called "comma-less"tags, as discussed below. Tags of word having commas are readily constructed from the minimally cross-hybridizing sets of words disclosed by Brenner in the several references cited above. Either comma-containing or comma-less tags may be used with the invention; however, comma-less tags are preferred, as they generate the maximum degree of instability in a duplex formed after any small (e.g. 1-3 nucleotide) shift of the tag and anti-tag out of perfect alignment, also sometimes referred to herein as a "change of phase."

Figure 4A:
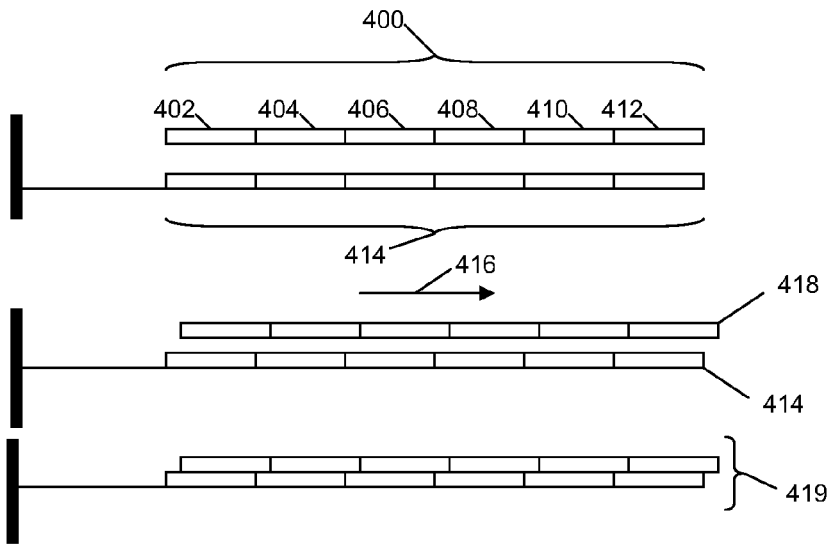
FIGS. 4A-4D illustrate combinatorial tags of words with and without commas (with "commas") and "comma-less"), and FIG. 4E lists melting temperatures of selected tags consisting of four words each having the comma-less property.

As mentioned above, in tags synthesized combinatorially from shorter oligonucleotide "words," stable duplexes may form between a tag and its complement, even though the "words" are not perfectly aligned. As illustrated in FIG. 4A, oligonucleotide tag (400) consisting of words (402), (404), (406), (408), (410) and (412) may align perfectly with its complement (414) to form a perfectly matched duplex. However, with some selections of words, there may be other tags (418) in the same repertoire that also form stable duplexes (419), even though the tag (418) is shifted (416), or out of alignment, by one or more bases with complement (414). The stability of such spurious pairings is very close to that of the perfectly aligned pairings, making it difficult to discriminate between correctly hybridized tags and incorrectly hybridized tags.

Figure 4B:
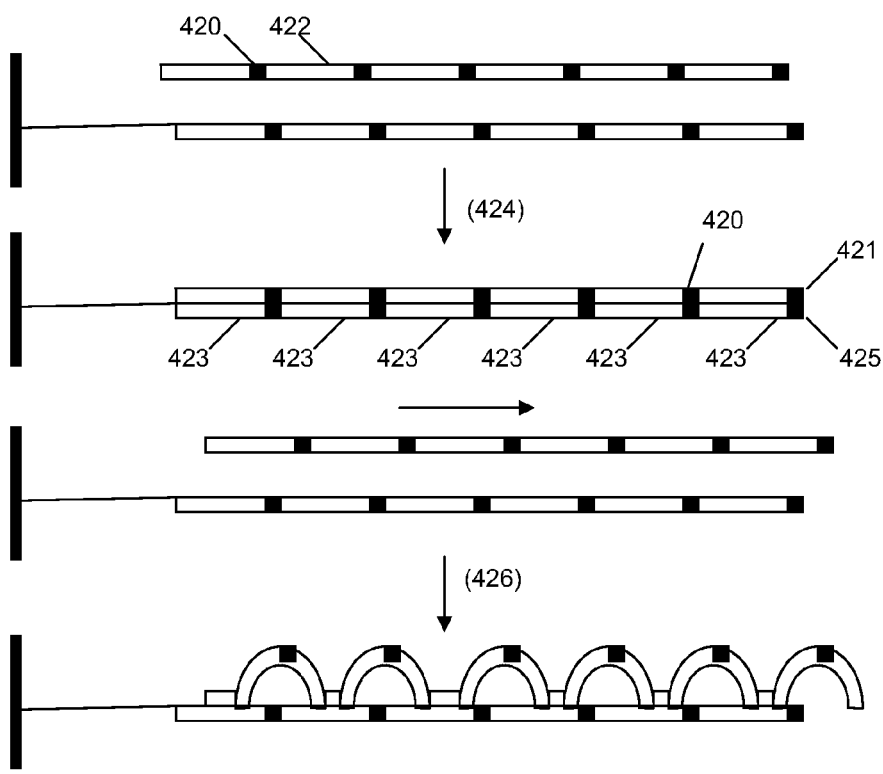

Such spurious hybridizations can be eliminated by designing tags that have large numbers of mismatches whenever the tag and its complement are shifted one or more bases away from the perfectly aligned configuration. As mentioned above, such designs can be accomplished by either introducing "commas" between words, or by designing words that inherently have the property that any shift out of perfect alignment introduces large numbers of stability-destroying mismatches. In its simplest form, "commas" may be one or more nucleotides (420) introduced between the words (422) of a tag, as illustrated in FIG. 4B. For example, the commas (420) of tag (421) may consist of G's, while the words (422) may consist of only A's, T's, and C's. Thus, for a perfectly matched duplex to form (i) the commas must be aligned, and (ii) the words of tag (421) must each be the complement of the words (423) of complement (425), when there is perfect alignment, a perfectly match duplex (424) is formed. If neither of these conditions is met, then no duplex will form, or if it does form (426), its stability will be vastly lower than that of the perfectly aligned and matched tags (424).

Figure 4C:
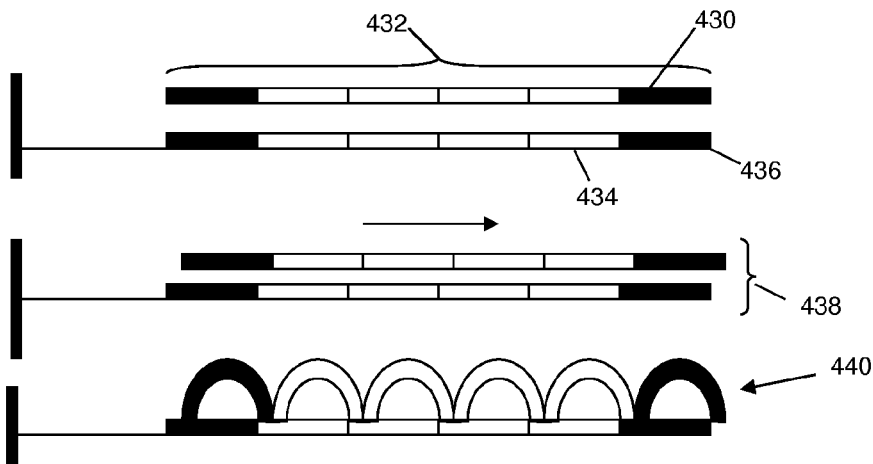

"Commas" may also take the form of words, as illustrated in FIG. 4C. Again, by way of example, the end words (430) of tag (432) may consist of G's, whereas the internal words (434) may consist of A's, C's, and T's. This constrains tag (432) and its complement (436) to be correctly aligned. As above, absence perfect alignment (438), the stability of any duplex (440) that may form will be vastly lower than that of a perfectly aligned tag and its complement.

Figure 4D:
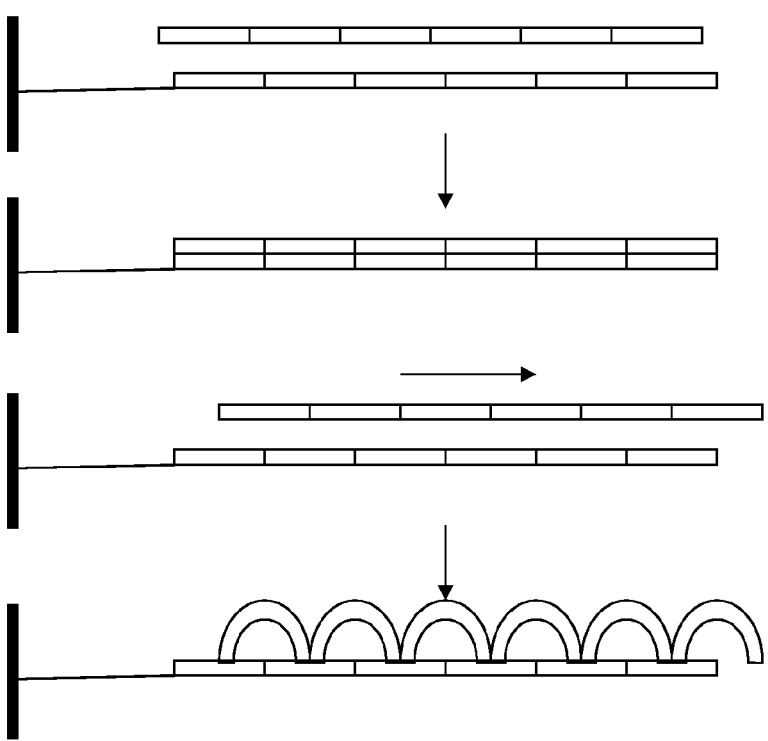

Finally, repertoires of tags without commas may be constructed from words that have the same properties as tags with commas. Such tags with the "comma-less" property are illustrated in FIG. 4D. That is, in order to form a perfectly matched duplex between a tag and a complement, the two must be perfectly aligned. Words for a repertoire of comma-less tags may be constructed in a wide variety of lengths, e.g. such words may have lengths in the range of from 4 to 10 nucleotides, and may consist of natural or non-natural nucleotides. In one aspect, words are construct from the four natural nucleotides, A, C, G, and T, whenever the resulting tags are operated on by enzymes. In another aspect, words may be constructed from nucleotides selected from the group consisting of A, C, G, T, and I, when the resulting tags (or anti-tags) are not processed by enzymes. Anti-tags synthesized on a solid phase support may typically be constructed from a wider variety of nucleotides than tags that are processed by enzymes. In one aspect of the invention, comma-less tags may be constructed from the following words.

Consider doublets of the four natural bases. Four sets of such doublets, 16 in all, can be defined as follows.

| I | II | III | IV |
|---|----|-----|-----|
| GT | CT | AT | AA |
| TG | TC | TA | TT |
| AC | AG | CG | CC |
| CA | GA | GC | GG |

In each set, all four differ in both positions from all the other members of the set, but when the four different sets are compared with each other, one base is held in common with one member of the other set. For example, in set I, eight different words can be created by combining doublets from set I with doublets from set II in the I-II order and the II-I order. Since each of these sets contain doublets that are the reverse complements of the other, the combinations are made such that none of I-II four-base words are the inverse complements of the II-I four-base words. Thus, if the I-II words are selected as follows: GTCT, TGTC, ACAG, and CAGA, then the II-I words can be defined only as follows:

| AGCA | or | AGGT |
| GAAC |    | GATG |
| CTTG |    | CTAC |
| TCGT |    | TCCA | an arrangement which conserves the constraint that the members of each set differs by three bases from any member of the same set. From the above sets, several sets of words for comma-less tags can be constructed. Taking the first two sets, an "A" to the end of each words of the first set, and a "T" to the end of each word of the second set to give the following:

| AGCAT | GTCTA |
| GAACT | TGTCA |
| CTTGT | ACAGA |
| TCGTT | CAGAA |

Although the same process does not work with sets III and IV above because in III the doublets are self-complementary, further sets of words can be created by switching the I-II into II-I and vice versa, and adding the bases as above, which gives:

| CTGTA | CAAGT |
| TCTGA | ACGAT |
| AGACA | TGCTT |
| GACAA | GTTCT |

For tags not used in enzymatic processing, such as anti-tags synthesized on a solid phase support, the following sets employing deoxyinosine may be employed:

| AICAT | GTCTA |
| GAACT | TGTCA |
| CTTGT | ACAGA |
| TCITT | CAGAA | and

| CTGTA | CAAGT |
| TCTGA | ACIAT |
| AGACA | TICTT |
| GACAA | GTTCT |

Further sets of words for constructing comma-less tags are listed in FIG. 4E.

Oligonucleotide Tags with No Repeat Words

As mentioned above, in some embodiments, it is desirable to decode oligonucleotide tags sequentially. This requires that the oligonucleotide tags be constructed without repeat words. Such oligonucleotide tags can be constructed as follows. Let set I of mutually discriminable di-words consist of GT, TG, CA, and AC, and set II of mutually discriminable di-words consist of GA, AG, CT, and TC. These are combined in two different ways to give two different groups (referred to herein as "languages") of four dilects, each containing eight words. Language A comprises words of the form: $S_I$-T-$S_{II}$ and $S_{II}$-A-$S_I$ and language B comprises words of the form: $S_I$-A-$S_I$ and $S_{II}$-T-$S_{II}$, where $S_I$ is a di-word selected from set I and $S_{II}$ is a di-word selected from set II. The A or T inserted between the di-words gives oligonucleotide tags constructed from such words the comma-less condition. Writing out the combinations, the following eight groups of eight-word sets are formed:

| Language A | | | |
|---|---|---|---|
| Dialect 1 | Dialect 2 | Dialect 3 | Dialect 4 |
| GTTGA | GTTAG | GTTCT | GTTTC |
| TGTAG | TGTCT | TGTTC | TGTGA |
| CATCT | CATTC | CATGA | CATAG |
| ACTTC | ACTGA | ACTAG | ACTCT |
| GAATG | GAACA | GAAAC | GAAGT |
| AGACA | AGAAC | AGAGT | AGATG |
| CTAAC | CTAGT | CTATG | CTACA |
| TCAGT | TCATG | TCACA | TCAAC |

| Language B | | | |
|---|---|---|---|
| Dialect 1 | Dialect 2 | Dialect 3 | Dialect 4 |
| GTAGT | GTATG | GTACA | GTAAC |
| TGATG | TGACA | TGAAC | TGAGT |
| CAACA | CAAAC | CAAGT | CAATG |
| ACAAC | ACAGT | ACATG | ACACA |
| CTTTC | CTTGA | CTTAG | CTTCT |
| TCTGA | TCTAG | TCTCT | TCTTC |
| GATAG | GATCT | GATTC | GATGA |
| AGTGT | AGTTC | AGTGA | GATAG |

Within each dialect, each word differs from the other seven words in 4 out of 5 bases. Within each language set A or B, words in one dialect differ from those in other dialects by at least two bases out of the 5, some differ by three and some by 4. Between languages A and B, the dialects differ by at least 1 of 5 bases, which is 20% discrimination and some differ by 2, 3, 4, and 5 bases. Thus, oligonucleotide tags can be constructed from them, either as a set of 4 from each of language A or language B, or as a full set of 8 from both. 4096 ($=8^4$) 4-word oligonucleotide tags can be constructed from language A (e.g. as A1-A2-A3-A4, where A1 is a word selected from dialect 1 of language A, A2 is a word selected from dialect 2 of language A, and so on). By using both language A and B, 16 million ($=8^8$) oligonucleotide tags can be generated (e.g. A1-A2-A3-A4-B1-B2-B3-B4, where A1-A4 are defined as above, and B1-B4 are defined equivalently). Note that in both cases, only one member is used from each dialect. There are no repeated words in the oligonucleotide tags thus constructed.

Tag Complements, Hybridization, and Readout

Preferably, tag complements are synthesized on the surface of a solid phase support, such as a microscopic bead or a specific location on an array of synthesis locations on a single support, e.g. a microarray, such that populations of identical, or substantially identical, sequences are produced in specific regions. That is, the surface of each support, in the case of a bead, or of each region, in the case of an array, is derivatized by copies of only one type of tag complement having a particular sequence. The population of such beads or regions contains a repertoire of tag complements each with distinct sequences. As used herein in reference to oligonucleotide tags, including hybridization tags, tag complements, ligation tags, and the like, the term "repertoire" means the total number of different tags or tag complements in a given set or population.

Solid phase supports containing tag complements may take a variety of forms, e.g. particulate, single-piece and planar, such as a glass slide, and may be composed of a variety of materials, e.g. glass, plastic, silicon, polystyrene, or the like. Particulate solid phase supports include microspheres, such as fluorescently labeled microspheres, e.g. Han et al, Nature Biotechnology, 19: 631-635 (2001); Kettman et al, Cytometry, 33: 234-243 (1998); quantum dots, and the like. In one aspect, hybridization tags are detected by hybridizing them to their complementary sequences on a microarray. Such microarrays may be manufactured by several alternative techniques, such as photo-lithographic optical methods, e.g. Pirrung et al, U.S. Pat. No. 5,143,854, Fodor et al, U.S. Pat. Nos. 5,800,992; 5,445,934; and 5,744,305; fluid channel-delivery methods, e.g. Southern et al, Nucleic Acids Research, 20: 1675-1678 and 1679-1684 (1992); Matson et al, U.S. Pat. No. 5,429,807, and Coassin et al, U.S. Pat. Nos. 5,583,211 and 5,554,501; spotting methods using functionalized oligonucleotides, e.g. Ghosh et al, U.S. Pat. No. 5,663,242; and Bahl et al, U.S. Pat. No. 5,215,882; droplet delivery methods, e.g. Caren et al, U.S. Pat. No. 6,323,043; Hughes et al, Nature Biotechnology, 19: 342-347 (2001); and the like. The above patents disclosing the synthesis of spatially addressable microarrays of oligonucleotides are hereby incorporated by reference. Microarrays used with the invention contain from 50 to 500,000 hybridization sites; or from 100 to 250,000 hybridization sites; or from 100 to 40,000 hybridization sites; and preferably, they contain from 100 to 32,000 hybridization sites; or from 100 to 20,000 hybridization sites; or from 100 to 10,000 hybridization sites.

Guidance for selecting conditions and materials for applying labeled oligonucleotide probes to microarrays may be found in the literature, e.g. Wetmur, Crit. Rev. Biochem. Mol. Biol., 26: 227-259 (1991); DeRisi et al, Science, 278: 680-686 (1997); Wang et al, Science, 280: 1077-1082 (1998); Duggan et al, Nature Genetics, 21: 10-14 (1999); Schena, Editor, Microarrays: A Practical Approach (IRL Press, Washington, 2000); Hughes et al (cited above); Fan et al, Genomics Research, 10: 853-860 (2000); and like references. These references are hereby incorporated by reference. Typically, application of hybridization tags to a solid phase support includes three steps: treatment with a pre-hybridization buffer, treatment with a hybridization buffer that includes the probes, and washing under stringent conditions. A pre-hybridization step is employed to suppress potential sites for non-specific binding of probe. Preferably, pre-hybridization and hybridization buffers have a salt concentration of between about 0.8-1.2 M and a pH between about 7.0 and 8.3. Preferably, a pre-hybridization buffer comprises one or more blocking agents such as Denhardt's solution, heparin, fragmented denature salmon sperm DNA, bovine serum albumin (BSA), SDS or other detergent, and the like. An exemplary pre-hybridization buffer comprises 6×SSC (or 6×SSPE), 5×Denhardt's solution, 0.5% SDS, and 100 µg/ml denatured, fragmented salmon sperm DNA, or an equivalent defined-sequence nucleic acid. Another exemplary pre-hybridization buffer comprises 6×-SSPE-T (0.9 M NaCl, 60 mM NaH2PO4, 6 mM EDTA (pH 7.4), 0.005% Triton X-100) and 0.5 mg/ml BSA. Pre-hybridization and hybridization buffers may also contain organic solvents, such as formamide to control stringency, tetramethylammonium chloride to negate base-specific effects, and the like. An exemplary hybridization buffer is SSPE-T. After hybridization, unbound and non-specifically bound oligonucleotide is removed by washing the detection support under stringent conditions. Preferably, stringency of the wash solution is controlled by temperature, organic solvent concentration, or salt concentration. More preferably, the stringency of the wash conditions are determined to be about 2-5° C. below the melting temperature of the isostringency probes at the salt concentration and pH of the wash solution. Preferably, the salt concentration of the wash solution is between about 0.01 to 0.1 M.

Exemplary hybridization procedures for applying labeled target sequence to a GenFlex™ microarray (Affymetrix, Santa Clara, Calif.) is as follows: denatured labeled target sequence at 95-100° C. for 10 minutes and snap cool on ice for 2-5 minutes. The microarray is pre-hybridized with 6×SSPE-T (0.9 M NaCl 60 mM NaH$_2$PO$_4$, 6 mM EDTA (pH 7.4), 0.005% Triton X-100)+0.5 mg/ml of BSA for a few minutes, then hybridized with 120 µL hybridization solution (as described below) at 42° C. for 2 hours on a rotisserie, at 40 RPM. Hybridization Solution consists of 3M TMACL (Tetramethylammonium. Chloride), 50 mM MES ((2-[N-Morpholino]ethanesulfonic acid) Sodium Salt) (pH 6.7), 0.01% of Triton X-100, 0.1 mg/ml of Herring Sperm DNA, optionally 50 pM of fluorescein-labeled control oligonucleotide, 0.5 mg/ml of BSA (Sigma) and labeled target sequences in a total reaction volume of about 120 µL. The microarray is rinsed twice with 1× SSPE-T for about 10 seconds at room temperature, then washed with 1×SSPE-T for 15-20 minutes at 40° C. on a rotisserie, at 40 RPM. The microarray is then washed 10 times with 6×SSPE-T at 22° C. on a fluidic station (e.g. model FS400, Affymetrix, Santa Clara, Calif.). Further processing steps may be required depending on the nature of the label(s) employed, e.g. direct or indirect. Microarrays containing labeled target sequences may be scanned on a confocal scanner (such as available commercially from Affymetrix) with a resolution of 60-70 pixels per feature and filters and other settings as appropriate for the labels employed. GeneChip Software (Affymetrix) may be used to convert the image files into digitized files for further data analysis.

Instruments for measuring optical signals, especially fluorescent signals, from labeled tags hybridized to targets on a microarray are described in the following references which are incorporated by reference: Stem et al, PCT publication WO 95/22058; Resnick et al, U.S. Pat. No. 4,125,828; Karnaukhov et al, U.S. Pat. No. ,354,114; Trulson et al, U.S. Pat. No. 5,578,832; Pallas et al, PCT publication WO 98/53300; Brenner et al, Nature Biotechnology, 18: 630-634 (2000); and the like. Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

When tag complements are attached to or synthesized on microbeads, a wide variety of solid phase materials may be used with the invention, including microbeads made of controlled pore glass (CPG), highly cross-linked polystyrene, acrylic copolymers, cellulose, nylon, dextran, latex, polyacrolein, and the like, disclosed in the following exemplary references: Meth. Enzymol., Section A, pages 11-147, vol. 44 (Academic Press, New York, 1976); U.S. Pat. Nos. 4,678,814; 4,413,070; and 4,046,720; and Pon, Chapter 19, in Agrawal, editor, Methods in Molecular Biology, Vol. 20, (Humana Press, Totowa, N.J., 1993). Microbead supports further include commercially available nucleoside-derivatized CPG and polystyrene beads (e.g. available from Applied Biosystems, Foster City, Calif.); derivatized magnetic beads; polystyrene grafted with polyethylene glycol (e.g., TentaGel™, Rapp Polymere, Tubingen Germany); and the like. Generally, the size and shape of a microbead is not critical; however, microbeads in the size range of a few, e.g. 1-2, to several hundred, e.g. 200-1000 µm diameter are preferable, as they facilitate the construction and manipulation of large repertoires of oligonucleotide tags with minimal reagent and sample usage. Preferably, glycidal methacrylate (GMA) beads available from Bangs Laboratories (Carmel, Ind.) are used as microbeads in the invention. Such microbeads are useful in a variety of sizes and are available with a variety of linkage groups for synthesizing tags and/or tag complements.

As mentioned above, in one aspect tag complements comprise PNAs, which may be synthesized using methods disclosed in the art, such as Nielsen and Egholm (eds.), Peptide Nucleic Acids: Protocols and Applications (Horizon Scientific Press, Wymondham, UK, 1999); Matysiak et al, Biotechniques, 31: 896-904 (2001); Awasthi et al, Comb. Chem. High Throughput Screen., 5: 253-259 (2002); Nielsen et al, U.S. Pat. No. 5,773,571; Nielsen et al, U.S. Pat. No. 5,766,855; Nielsen et al, U.S. Pat. No. 5,736,336; Nielsen et al, U.S. Pat. No. 5,714,331; Nielsen et al, U.S. Pat. No. 5,539,082; and the like, which references are incorporated herein by reference. Construction and use of microarrays comprising PNA tag complements are disclosed in Brandt et al, Nucleic Acids Research, 31(19), e119 (2003).

Tagging Polynucleotides

As mentioned above, an important feature of the invention is attaching oligonucleotide tags to polynucleotides, such as fragments from a genome. For simultaneous analysis of fragments from many different genomes, fragments from each different genome have the same oligonucleotide tag attached. In this manner, after a particular analytical operation has taken place on a mixture, such as extending a primer, capturing extended primers, or the like, the result on a particular fragment, or subset of fragments, may be assessed by using their respective oligonucleotide tags, e.g. by labeling, copying, and hybridizing them to a readout platform, such as a microarray. Below, an example is provided for generating a population of genomic fragments wherein fragments from each different genome have a different oligonucleotide tag attached that is comprised of oligonucleotide subunits, or words.

In one aspect of the invention, all fragments of each genome of a population of genomes are labeled with one combination of words selected from a set of eight 5-nucleotide words, or subunits. Thus, when oligonucleotide tags comprise four such words, a repertoire of 4096 oligonucleotide tags is formed; when oligonucleotide tags comprise five such words, a repertoire of 32,768 ($=8^5$) oligonucleotide tags is formed; and so on. Once each genome has a unique tag, then common-sequence fragments, e.g. a restriction fragment from a particular locus, can be selected using the method of the invention. The tags may then be used to convey information about the fragments, e.g. the identity of a nucleotide at a particular locus, to a hybridization array for a readout. One of ordinary skill in the art understands that the selection of 5-word oligonucleotide tags of five nucleotides each and the use of commaless tags are design choices that may be varied depending on the goals and constraints of any particular application. In one embodiment the following eight-word minimally cross-hybridizing set may be used to construct the above repertoire. As described below, preferably, each word is cloned in a plasmid with additional elements for aiding in the construction of oligonucleotide tags.

```
        AGCAT           GTCTA

GAACT           TGACA

TCTGT           ACGAA

CTGTT           CATCA
```

Using these words, 64 di-words are prepared in separate plasmids as described in Brenner and Williams (cited above), which is incorporated by reference.

A. Single-Word Library and Counting Array Element.

In one embodiment, the single word library contains a ten-base sequence [G/T; G/T; A/T]$_3$G/T, where "x/T" is an equal mixture of the two bases "x" and "T" at a particular locus. This element encodes a repertoire of 1024 ($=2^{10}$) different sequences that permits sequences to be counted by hybridization of copies of the sequence to an array of complementary sequences, i.e. a "counting" array. This element is referred to herein as the "Counting Array" or "CAR" element. In this embodiment, about 30 copies of each genome are tagged and each is labeled with one unique sequence. Thus, if any sorted molecule is found to have a unique sequence for this array, it is not a genome difference that should have multiple sequences, and is likely to represent an error in the process which has resulted in an altered molecule. Note that however much any fragment is amplified that it will always possess the original sequences in the counting array, preserving cardinality as distinct from the concentration of DNA.

A plasmid having the following characteristics is constructed: (i) no SapI site, and (ii) a sequence of restriction sites:

```
    GGGCCC    ...    AGGCCT    ...    GGTACC (ApaI)           (BspEI)          (KpnI)
```

These sites each have "GG" which is absent from tags constructed from the words of the above set. Next for each word the strands of following element are synthesized (SEQ ID NO: 5):

```
    5'-pCNNNNNNNNNNNGCATCNNNNN[WORD]A

3'-CCGGGNNNNNNNNNNNCGTAGNNNNN[WORD]TCCGGp (Sfa N1)
``` where lower case "p" represents a phosphate group. After annealing the strands, the element is cloned into the above plasmid by cleaving with ApaI and Bsp E1. Several plasmids are picked for each word and the clones are sequenced to check the accuracy of the sequence, after which one is selected for use in tag construction. Elements for the "counting" array are synthesized and also a second primer binding site which will be required for later amplification. After synthesis, the following structure is obtained (SEQ ID NO: 6):

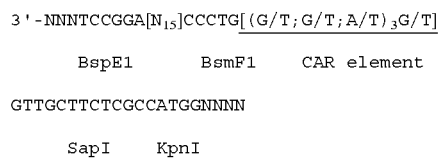

Using the primer "5'-NNNAGGCCT[N$_{15}$]GGGAC" (SEQ ID NO: 7) the above is copied, cleaved with KpnI and BspE1, and cloned into each of the single-word plasmids. $10^4$ clones of each are isolated to make sure that all the sequences of the counting array are in the library.

This embodiment is designed to attach tags to fragments generated by cleaving with the "↓GATC" family of restriction endonucleases. These enzymes permit the generation of the fragments of several different lengths:

| Enzyme | Recognition Site | Average Fragment Length |
|---|---|---|
| Bam HI | G↓GATCC | 4 Kb |
| Bam HI + BglII | G↓GATCC + G↓GATCT | 2 Kb |
| Bst YI | R↓GATCY | 1 Kb |
| Sau 3a | ↓GATC | 256 bp |

All of these leave the same end when cleaved, namely:

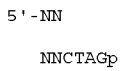

where "p" is a phosphate group. This may be filled in with a single dGTP to give a three-base overhang:

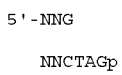

After such filling, polynucleotides or cloning vectors cut with SapI (underlined below), which leaves the following ends:

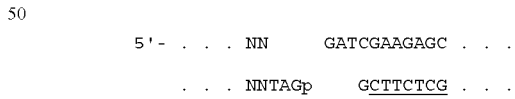

permits efficient and directional cloning of fragments.

The final construct has the following structure:

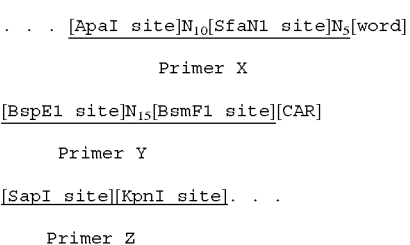

were "N" are arbitrarily selected nucleotides and "CAR" is a counting array element, as described above.

B. Double-Word Libraries.

Here a library of 64 vectors is disclosed each containing one of the 64 possible two-word, or "di-word," concatenations of words from the 8-word library flanked by primer binding sites. This double-word library is then used essentially as described in Brenner and Williams (cited above) to construct oligonucleotide tags. In this embodiment, the first flanking primer binding site is that shown above as "Primer X," and the other contains a recognition site for FokI, are then combined (532) to form mixture (550) of tagged genomes. More specifically, the procedure may be carried out with the following steps.

About 1 ng of human DNA (about 30 copies of the haploid genome) is digested with Bst Y1 to give fragments of an average size of 1 Kb, after which ends are filled in with dGTP to give 3-base ends as described above.

The eight single word libraries, labeled A-H, are amplified and cut with SapI to generate the following single-word fragment:

```
[ApaI site]N10[SfaN1 site]N5[word][BspE1 site]N15[BsmF1 site][CAR]

[ApaI site]N10[SfaN1 site]N5[word][BspE1 site]N15[BsmF1 site][CAR]CTAp

Primer X                                                    Primer Y
```

5'-GGATG(9/13), which contains "GG" and therefore cannot cut any of the words described above.

The following vector elements are synthesized (SEQ ID NO: 8):

```
5'-pCN10[SfaN1 site]N5[word 1][word 2]N8CATCC
``` and (SEQ ID NO: 9):

```
3'-CCGGGN10[SfaN1 site]N5[word 1][word 2]
                                         N9GTAGGCTAG
``` where it is understood that the "word 1" and "word 2" refer to both word sequences and their respective complements. After annealing the above fragments to form a doublestranded element, it is cloned into a plasmid digested with ApaI and BamHI. To assure the accuracy of the incorporation, several clones of each "double word" vector are selected and sequenced. Copies of di-words may be conveniently obtained by PRC using a biotinylated X primer and another primer.

C. Tagging Genome Fragments.

In this example, a procedure is disclosed for attaching oligonucleotide tags to up to 4096 different genome for simultaneous analysis in accordance with the invention. The procedure is outlined in FIG. 5. Sixty-four groups of 64 samples are formed that each contain fragments from a single genome, each group of 64 being represented in the figure by arrays (502), (504), and (506) of 64 dots. This is base tier (500) of samples where fragments from each genome may be identified by its position in such a 64-element array, which may correspond to a well in a multi-well plate, a tube in a rack of tubes, or the like. Intermediate tier of submixtures (510) is formed by attaching a different two-word tag to each different genome, as described below. The two-word tag identifies a genome fragment by giving its location within the 64-element array of samples. To each group of two-word tagged fragments, indicated as $g_1AA$ to $g_{64}HH$; $g_{65}AA$ to $g_{128}HH$; and so on, a different tag A through H is attached and combined (514) to form the first mixture (520) in intermediate tier of mixtures (530). The rest of the groups of 64 genomes are treated the same to produce addition mixtures of intermediate tier (530), e.g. mixtures containing $g_{513}AA$ to $g_{576}HH$; $g_{577}AA$ to $g_{640}HH$; and so on, have words added and are combined (516) to form submixture (522); and so on, until the final mixtures in intermediate tier (510) (not shown) are tagged and combined (518). Tagged fragments in submixtures (520) to (524) each have a different word attached and 64 genomes are tagged in one batch as follows. 64 reaction vessels are arranged in an 8×8 array wherein each row, 1-8, contains 8 vessels labeled A-H. To each vessel a different Bst YI-digested genome is added, after which a different single-word fragment, A-H, is added to vessels 1-8, in each row to give the following array of reaction vessels with the following single-word fragments:

| Row | 1-tube/cell of table (8 tubes/row or 64 tubes in total) | | | | | | | |
|---|---|---|---|---|---|---|---|---|
| 1 | $g_1A$ | $g_2B$ | $g_3C$ | $g_4D$ | $g_5E$ | $g_6F$ | $g_7G$ | $g_8H$ |
| 2 | $g_9A$ | $g_{10}B$ | $g_{11}C$ | $g_{12}D$ | $g_{13}E$ | $g_{14}F$ | $g_{15}G$ | $g_{16}H$ |
| 3 | $g_{17}A$ | $g_{18}B$ | $g_{19}C$ | $g_{20}D$ | $g_{21}E$ | $g_{22}F$ | $g_{23}G$ | $g_{24}H$ |
| 4 | $g_{25}A$ | $g_{26}B$ | $g_{27}C$ | $g_{28}D$ | $g_{29}E$ | $g_{30}F$ | $g_{31}G$ | $g_{32}H$ |
| 5 | $g_{33}A$ | $g_{34}B$ | $g_{35}C$ | $g_{36}D$ | $g_{37}E$ | $g_{38}F$ | $g_{39}G$ | $g_{40}H$ |
| 6 | $g_{41}A$ | $g_{42}B$ | $g_{43}C$ | $g_{44}D$ | $g_{45}E$ | $g_{46}F$ | $g_{47}G$ | $g_{48}H$ |
| 7 | $g_{49}A$ | $g_{50}B$ | $g_{51}C$ | $g_{52}D$ | $g_{53}E$ | $g_{54}F$ | $g_{55}G$ | $g_{56}H$ |
| 8 | $g_{57}A$ | $g_{58}B$ | $g_{59}C$ | $g_{60}D$ | $g_{61}E$ | $g_{62}F$ | $g_{63}G$ | $g_{64}H$ | where "$g_K$" is a fragment from genome K

The single-word fragments are ligated to the genome fragments to give genome fragments having single-word fragments on both ends. These fragments are processed as follows so that a single word is on only one end. First, the reaction constituents from every vessel in each row are pooled so that eight mixed samples are obtained.

| Row (Tube) | Resulting Mixtures (1-tube/row) | | | | | | | |
|---|---|---|---|---|---|---|---|---|
| 1 | $g_1A$ | $g_2B$ | $g_3C$ | $g_4D$ | $g_5E$ | $g_6F$ | $g_7G$ | $g_8H$ |
| 2 | $g_9A$ | $g_{10}B$ | $g_{11}C$ | $g_{12}D$ | $g_{13}E$ | $g_{14}F$ | $g_{15}G$ | $g_{16}H$ |
| 3 | $g_{17}A$ | $g_{18}B$ | $g_{19}C$ | $g_{20}D$ | $g_{21}E$ | $g_{22}F$ | $g_{23}G$ | $g_{24}H$ |
| 4 | $g_{25}A$ | $g_{26}B$ | $g_{27}C$ | $g_{28}D$ | $g_{29}E$ | $g_{30}F$ | $g_{31}G$ | $g_{32}H$ |
| 5 | $g_{33}A$ | $g_{34}B$ | $g_{35}C$ | $g_{36}D$ | $g_{37}E$ | $g_{38}F$ | $g_{39}G$ | $g_{40}H$ |
| 6 | $g_{41}A$ | $g_{42}B$ | $g_{43}C$ | $g_{44}D$ | $g_{45}E$ | $g_{46}F$ | $g_{47}G$ | $g_{48}H$ |
| 7 | $g_{49}A$ | $g_{50}B$ | $g_{51}C$ | $g_{52}D$ | $g_{53}E$ | $g_{54}F$ | $g_{55}G$ | $g_{56}H$ |
| 8 | $g_{57}A$ | $g_{58}B$ | $g_{59}C$ | $g_{60}D$ | $g_{61}E$ | $g_{62}F$ | $g_{63}G$ | $g_{64}H$ |

The DNA of each of the eight vessels is denatured and Primer Y (pAGGCCTN15GGGAC) (SEQ ID NO: 10) is added to prime the 3' tag sequence of each of the single strands as follows (SEQ ID NO: 11 AND SEQ ID NO: 12):

```
AGGCCTN15GGGAC

TCCGGAN15CCCTG[CAR]CTAG[fragment]CTAG[CAR]

GTCCC . . .
```

The primer is extended using 5-Me-dCTP to give the following (SEQ ID NO: 13 AND SEQ ID NO: 14):

```
AGGCCTN15GGGAC[CAR]GATC(Me)[fragment]GATC(Me)

[CAR]GTC(Me)C(Me)C(Me) . . .

TCCGGAN15CCCTG[CAR]CTAG    [fragment]CTAG

[CAR]CAG    G    G    . . .
```

All of the BsmF1 sites of the fragments are protected by half methylation, except for the site to the left of the tag. When the fragments are cleaved with BsmF1, the left tag is removed up to the "GATC" site, leaving the following (SEQ ID NO: 15):

```
            ↓
... GGGAC[CAR]GATC[fragment] ...
... CCCTG[CAR]CTAG[fragment] ...
            ↑
``` which results in the following:

```
GATC [fragment]GATC[CAR][BsmF1 site][Primer Y]

[word]N5[SfaN1 site][Primer X]

[fragment]CTAG[CAR][BsmF1 site][Primer Y]

[word]N5[SfaN1 site][Primer X]
```

The "GATC" overhang is filled in with dGTP and ligated to the following adaptor containing a primer binding site for sequencing (SEQ ID NO: 16):

```
       N20GC^Me  ATCAG

N20CG    TAGTCTAGp
```

The methylated C in the upper strand protects the lefthand site while the right hand portion of the fragments are manipulated. Words are added as follows. First, the C's of the bottom strand are replaced with 5-methyl-C's. This is accomplished by denaturing the above fragments, priming with a biotinylated Primer X (5'-biotin-GGGCCCN10[Sfa N1 site]N5), copying with 5-Me-CTP, and removing the strands with avidinated support. The fragments are released by cleaving with Sfa N1 to give in each of the eight vessels the sequences:

```
[fragment]GATC[CAR][Primer Y]W

[fragment]CTAG[CAR][Primer Y]WWWWWp
``` where all eight words are represented in the overhang and "W" represents a nucleotide of a word or its complement. Next the di-word libraries are pooled, cleaved with FokI, then ligated to the above fragment to add the next word. The process is continued as outlined below until the desired number of words is added to the genomic fragments to complete the tags. Thus, by this method, 64 genomes at a time may be tagged.

Returning to the table immediately above, in each of the sixty-four 64-genome collections, a different word is added to each different row, e.g. A→Row 1, B→Row 2, etc., to produce the following mixtures:

| Row (Tube) | Resulting Mixtures | | | | | | | |
|---|---|---|---|---|---|---|---|---|
| 1 | $g_1$AA | $g_2$BA | $g_3$CA | $g_4$DA | $g_5$EA | $g_6$FA | $g_7$GA | $g_8$HA |
| 2 | $g_9$AB | $g_{10}$BB | $g_{11}$CB | $g_{12}$DB | $g_{13}$EB | $g_{14}$FB | $g_{15}$GB | $g_{16}$HB |
| 3 | $g_{17}$AC | $g_{18}$BC | $g_{19}$CC | $g_{20}$DC | $g_{21}$EC | $g_{22}$FC | $g_{23}$GC | $g_{24}$HC |
| 4 | $g_{25}$AD | $g_{26}$BD | $g_{27}$CD | $g_{28}$DD | $g_{29}$ED | $g_{30}$FD | $g_{31}$GD | $g_{32}$HD |
| 5 | $g_{33}$AE | $g_{34}$BE | $g_{35}$CE | $g_{36}$DE | $g_{37}$EE | $g_{38}$FE | $g_{39}$GE | $g_{40}$HE |
| 6 | $g_{41}$AF | $g_{42}$BF | $g_{43}$CF | $g_{44}$DF | $g_{45}$EF | $g_{46}$FF | $g_{47}$GF | $g_{48}$HF |
| 7 | $g_{49}$AG | $g_{50}$BG | $g_{51}$CG | $g_{52}$DG | $g_{53}$EG | $g_{54}$FG | $g_{55}$GG | $g_{56}$HG |
| 8 | $g_{57}$AH | $g_{58}$BH | $g_{59}$CH | $g_{60}$DH | $g_{61}$EH | $g_{62}$FH | $g_{63}$GH | $g_{64}$HH |

These are combined to form a mixture designated as $g_{1-64}$ (AA-HH), where "AA-HH" means all 64 di-words from AA to HH. The same operation is separately carried out for every one of the sixty-four batches of 64 genomes each, i.e. genomes 65-128, 129-192, . . . and 448-512 to give the following 8 mixtures:

$g_{1-64}$ (AA-HH)

$g_{65-128}$ (AA-HH)

$g_{129-192}$ (AA-HH)

$g_{193-256}$ (AA-HH)

$g_{257-320}$ (AA-HH)

$g_{321-384}$ (AA-HH)

$g_{385-448}$ (AA-HH)

$g_{449-512}$ (AA-HH)

Figure 5:
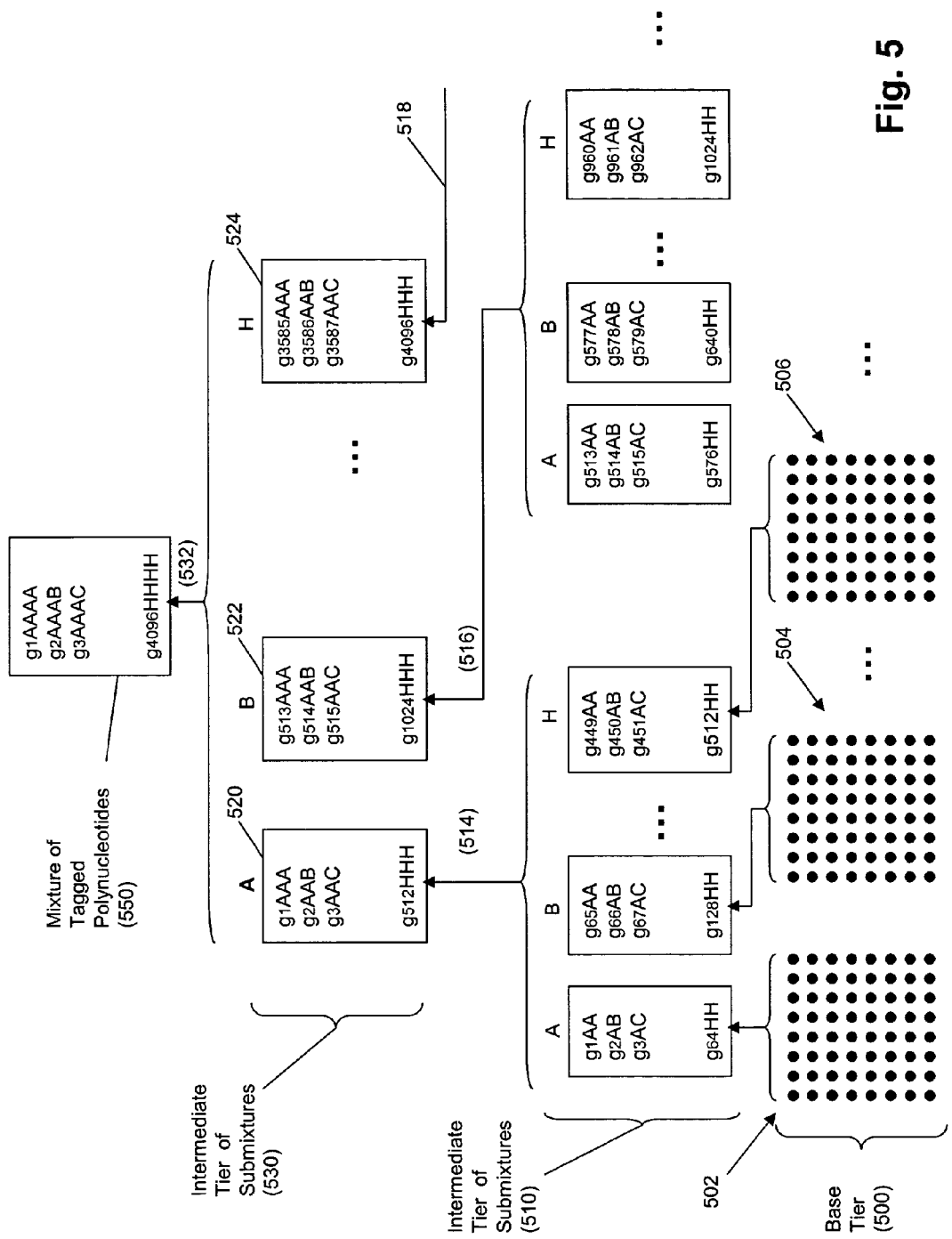
FIG. 5 illustrates tagging of polynucleotides by successive addition of oligonucleotide subunits, or "words."

As above, a different word is attached to each fragment in each of the different mixtures to give the following:

| Row (Tube) | Operation | Resulting Mixtures |
|---|---|---|
| 1 | A→ $g_{1-64}$ (AA-HH) | $g_{1-64}$ (AAA-HHA) |
| 2 | B→ $g_{65-128}$ (AA-HH) | $g_{65-128}$ (AAB-HHB) |
| 3 | C→ $g_{129-192}$ (AA-HH) | $g_{129-192}$ (AAC-HHC) |
| 4 | D→ $g_{193-256}$ (AA-HH) | $g_{193-256}$ (AAD-HHD) |
| 5 | E→ $g_{257-320}$ (AA-HH) | $g_{257-320}$ (AAE-HHE) |
| 6 | F→ $g_{321-384}$ (AA-HH) | $g_{321-384}$ (AAF-HHF) |
| 7 | G→ $g_{385-448}$ (AA-HH) | $g_{385-448}$ (AAG-HHG) |
| 8 | H→ $g_{449-512}$ (AA-HH) | $g_{449-512}$ (AAH-HHH) | where "AAA-HHH" means all $8^3$ (=512) tri-words from AAA to HHH. Again, a different word is attached to each fragment in each of the different three-word tagged fragment mixtures, which are then combined to form the final mixture (550), as shown in FIG. 5.

The following is claimed:

1. A method of sequencing comprising:
   sequencing a plurality of cDNAs, wherein the cDNAs are obtained from a plurality of different sources, and:
   (a) each of the cDNAs comprises: (i) a tag that indicates from which source a cDNA is derived and (ii) separate from the tag, a binding site for a sequencing primer;
   (b) the sequencing is done using the sequencing primer; and
   (c) the cDNAs have been selected from a pooled cDNA sample;
   to obtain, for each of the sequenced cDNAs, the nucleotide sequence of the tag associated with the cDNA and the nucleotide sequence of at least a portion of a cDNA.

2. The method of sequencing of claim 1, further comprising identifying the source of the cDNA using the sequence of the tag.

3. The method of sequencing of claim 1, wherein the different sources are different human individuals.

4. The method of sequencing of claim 1, wherein the cDNAs in the pooled cDNA sample are from 50 to 10,000 different sources.

5. The method of sequencing of claim 1, wherein the tag is from 2 to 18 nucleotides in length.

6. The method of sequencing of claim 1, wherein the cDNA is in the range of 100 to 300 nucleotides in length.

7. The method of sequencing of claim 1, wherein the method further comprises analyzing the sequences to identify a sequence variation.

8. The method of sequencing of claim 1, wherein the cDNAs are made by the following process:
   (i) pooling a plurality of samples to make a pooled sample; and
   (ii) selecting tagged cDNAs from the pooled sample, wherein the tagged cDNAs correspond to one or more genes, thereby producing the plurality of cDNAs that are sequenced.

9. The method of sequencing of claim 8, wherein the selecting is done by hybridization to a probe that is immobilized to a solid support.

10. The method of sequencing of claim 8, wherein the selecting is done by hybridization to a biotinylated probe that is captured by a solid support.

11. The method of sequencing of claim 8, wherein the selecting is done by exonuclease digestion of non-circularized probes.

12. The method of sequencing of claim 8, wherein the selecting is done by template-driven ligation.

13. The method of sequencing of claim 8, wherein the selecting is done by template-driven strand extension.

* * * * *